(12) United States Patent
Moradian

(10) Patent No.: US 12,577,558 B2
(45) Date of Patent: Mar. 17, 2026

(54) NEXT GENERATION SEQUENCING

(71) Applicant: MORAVA INC., Glendale, CA (US)

(72) Inventor: Mike Mkhitar Moradian, Glendale, CA (US)

(73) Assignee: MORAVA INC., Glendale, CA (US)

( * ) Notice: Subject to any disclaimer, the term of this patent is extended or adjusted under 35 U.S.C. 154(b) by 134 days.

(21) Appl. No.: 18/446,362

(22) Filed: Aug. 8, 2023

(65) Prior Publication Data

US 2024/0026349 A1    Jan. 25, 2024

Related U.S. Application Data

(60) Division of application No. 18/061,825, filed on Dec. 5, 2022, now Pat. No. 12,129,464, which is a continuation of application No. PCT/US2021/055477, filed on Oct. 18, 2021.

(60) Provisional application No. 63/093,602, filed on Oct. 19, 2020.

(51) Int. Cl.
    *C12N 15/10*       (2006.01)
    *C12Q 1/6806*      (2018.01)
(52) U.S. Cl.
    CPC ....... *C12N 15/1093* (2013.01); *C12Q 1/6806* (2013.01)
(58) Field of Classification Search
    CPC .......................... C12N 15/1093; C12Q 1/6806
    USPC .......................................................... 506/4
    See application file for complete search history.

(56) References Cited

U.S. PATENT DOCUMENTS

2016/0152972 A1* 6/2016 Stapleton ............. C12Q 1/6806
                                                   506/4
2017/0247689 A1    8/2017 Brown

FOREIGN PATENT DOCUMENTS

WO    WO-2016161236 A1 * 10/2016 ........... C12Q 1/6869
WO        2018053070 A1    3/2018
WO        2022086880 A     4/2022

OTHER PUBLICATIONS

Alkan et al. "Limitations of next-generation genome sequence assembly." Nat Methods., 2011, vol. 8(1), pp. 61-65.
Boutigny et al. "Targeted Next Generation Sequencing to study insert stability in genetically modified plants." Nature, Scientific Reports, 2019, vol. 9(2308), pp. 1-9.
Casas et. al., "Evaluation of Different Amplification Protocols for Use in Primer-Extension Preamplification.", Bio Techniques., 1996, vol. 20, pp. 219-225.
Chawla et al. "An atlas of RNA base pairs involving modified nucleobases with optimal geometries and accurate energies." Nucleic Acids Research, 2015, vol. 43(14), pp. 6715-6729.).
Durand et al. "Oligothymidylates covalently linked to an acridine derivative and with modified phosphodiester backbone: circular dichroism studies of their interactions with complementary sequences." Nucleic Acids Research, 1989, vol. 17(5), pp. 1823-1837.

(Continued)

*Primary Examiner* — Aaron A Priest
*Assistant Examiner* — Randi Lynn Beil
(74) *Attorney, Agent, or Firm* — Intelink Law Group, PC; Susan W. Gorman

(57)    ABSTRACT

An improved method for Next Generation Sequencing which relies on the presence of the same distinct unique molecular identifier (UMI) located at each end of a linear nucleic acid molecule so that sequence reads of approximately 2 kb or longer are obtained, and which allows generation of a genomic map without the need of a reference sequence.

14 Claims, 10 Drawing Sheets

Specification includes a Sequence Listing.

(56) References Cited

OTHER PUBLICATIONS

Ghosh et al. "Transformation of animal genomics by next-generation sequencing technologies: a decade of challenges and their impact on genetic architecture." Critical Reviews in Biotechnology, 2018, vol. 38(8), pp. 1157-1175.

Gladstone Institutes, "Combination of three gene mutations results in deadly human heart disease." Science Daily, 2019, vol. 364 (6443), pp. 865-870.

Hu et al. "Advances in Integrating Genomics and Bioinformatics in the Plant Breeding Pipeline." Agriculture, 2018, vol. 8(75), pp. 1-18.

Johnson et al. "Evaluation of 16S rRNA gene sequencing for species and strain-level microbiome analysis." Nature Communications, 2019, vol. 10(5029), pp. 1-11.

Kishore, A. and Petrek, M., "Next-Generation Sequencing Based HLA Typing: Deciphering Immunogenetic Aspects of Sarcoidosis." Front. Genet., 2018, vol. 9(503), pp. 1-20.

Liang, Y. and Wnuk, S.F., "Modification of Purine and Pyrimidine Nucleosides by Direct C—H Bond Activation." Molecules, 2015, vol. 20(3), pp. 4874-4901.

Liao et al. "Current challenges and solutions of de novo assembly." Quantitative Biology, 2019, vol. 7(2), pp. 90-109.

Lorenz, T. C., "Polymerase Chain Reaction: Basic Protocol Plus Troubleshooting and Optimization Strategies." Journal of Visualized Experiments. 63, 2012, p. 1-15. [online], [retrieved on Jun. 23, 2023]. Retrieved from the Internet: <URL:htps://www.ncbi.nlm.nih.gov/pmc/articles/PMC4846334/>(Year: 2012).

Lynch et al. "Translating the gut microbiome: ready for the clinic?" Nature Reviews Gastroenterology & Hepatology, 2019, vol. 16, pp. 656-661.

Mack et al. "Comprehensive genetic diagnosis of acute myeloid leukemia by next-generation sequencing." Haematologica, 2019, vol. 104(2), pp. 277-287.

Mantere et al. "Long-Read Sequencing Emerging in Medical Genetics." Frontiers in Genetics, 2019, vol. 10(426), pp. 1-14.

Markham et al. "CNspector: a web-based tool forvisualisation and clinical diagnosis of copy number variation from next generation sequencing." Scientific Reports, 2019, vol. 9(6426), pp. 1-9.

Maxwell et al. "KaryoScan: abnormal karyotype detection from whole-exome sequence." bioRxiv preprint, 2017, pp. 1-4.

McCarthy, M.I. and Macarthur, D.G., "Human disease genomics: from variants to biology." Genome Biology, 2017, vol. 18(20), pp. 1-3.

Menchise et al. "Insights into peptide nucleic acid (PNA) structural features: The crystal structure of a D-lysine-based chiral PNA-DNA duplex." PNAS, 2003, vol. 100(21), pp. 12021-12026.

New England Biolabs. "Guidelines for PCR Optimization using Phusion RT-PCR Kit Protocol." [online] [retrieved on Jun. 23, 2023]. Retrieved from the Internet <URL.htps://web.archive.org/web/20150922154511/https//www.neb.com/protocols/2012/06/01./guidelines-for-per-optimization-using-phusion-rt-pcr-kit (Year: 2015).

Nordlund et al. "Refined detection and phasing of structural aberrations in pediatric acute lymphoblastic leukemia by linked-read whole-genome sequencing." Scientific Reports, 2020, vol. 10(2512), pp. 1-10.

Park et al. "Detection of chromosome structural variation by targeted next-generation sequencing and a deep learning application." Scientific Reports, 2019, vol. 9(3644), pp. 1-9.

Posey, J.E. "Genome sequencing and implications for rare disorders." Orphanet Journal of Rare Diseases, 2019, vol. 14(153), pp. 1-10.

Raszek et al. "Use of Genomic Tools to Improve Cattle Health in the Context of Infectious Diseases." Front. Genet., 2016, vol. 7(30), pp. 1-15.

Sanger et al. "DNA sequencing with chain-terminating inhibitors." PNAS, 1977, vol. 74, No. 12, pp. 5463-5467.

Sohn, J. and Nam, J., "The present and future of de novo whole-genome assembly." Briefings in Bioinformatics, 2018, vol. 19(1), pp. 23-40.

Wang et al. "Assessment of 16S rRNA gene primers for studying bacterial community structure and function of aging flue cured tobaccos." AMB Expr, 2018, vol. 8(182), pp. 1-9.

Xu et al. "Detecting trisomy in products of conception from first-trimester spontaneous miscarriages by next-generation sequencing (NGS)." Medicine, 2020), vol. 99(5), pp. 1-7.

Final Office Action issued in corresponding United States parent U.S. Appl. No. 18/061,825, office action issued on Oct. 26, 2023.

International Search Report issued for PCT application No. PCTUS21/55477 which issued on Feb. 4, 2022.

Non-Final Office Action issued in corresponding United States parent U.S. Appl. No. 18/061,825, office action issued on Jul. 10, 2023.

* cited by examiner

1. Isolate and fragment to an average of 6 kb gDNA, cDNA, and/or RNA

2. Attach adapters having the form $nt_n dU_n$ – UMI – $dU_n nt_n$

3. Fragment to 3 kb and self-ligate

4. USER+Fill-in

5. Adapter Ligation

6. Random N Primer Extension

7. Final PCR

8. NGS

1. Isolate and fragment to an average of 6 kb gDNA, cDNA, and/or RNA

2.Attach nt$_n$dU$_n$ – UMI – dU$_n$nt$_n$adapters; f

3. Fragment to 3 kb and self-ligate

4. Fragmentation

5.USER enzyme treatment + fill-in and end repair/A-tail

6. Attach Illumina Adapters

6. PCR

7. NGS

Adapters $nt_n dU_n - UMI - dU_n nt_n$

5'P- UCUNNNNNNNNNNNNACAT - 3'OH (SEQ ID NO:1)

OH 3'- TAGANNNNNNNNNNNNUGU - 5'P  (SEQ ID NO:2)

| Name | Start_1 | End_1 | Start_2 | End_2 | 5p | 3p | InsertSize | Extension |
|---|---|---|---|---|---|---|---|---|
| M01558:36:000000000JKB76:1:2104:4342:14691 | 26456 | 26607 | 26090 | 26178 | 26090 | 26607 | 517 | 63 |
| M01558:36:000000000JKB76:1:2104:4363:14695 | 26456 | 26607 | 26090 | 26241 | 26090 | 26607 | | |
| M01558:36:000000000JKB76:1:2112:21407:16164 | 47502 | 47653 | 47128 | 47279 | 47128 | 47653 | 525 | 80 |
| M01558:36:000000000JKB76:1:1105:16975:16638 | 47582 | 47733 | 47208 | 47279 | 47208 | 47733 | | |
| M01558:36:000000000JKB76:1:2113:14509:27414 | 27668 | 27819 | 27208 | 27359 | 27208 | 27819 | 611 | 79 |
| M01558:36:000000000JKB76:1:2113:14516:27433 | 27668 | 27819 | 27208 | 27289 | 27208 | 27819 | | |
| M06418:138:000000000JK9FJ:1:1107:23216:19477 | 7472 | 7623 | 8072 | 8116 | 7472 | 8116 | 644 | 106 |
| M06418:138:000000000JK9FJ:1:1107:23196:19486 | 7472 | 7623 | 7966 | 8116 | 7472 | 8116 | | |
| M01558:36:000000000-JKB76:1:1108:12619:6991 | 24048 | 24199 | 24625 | 24706 | 24048 | 24706 | 658 | 79 |
| M01558:36:000000000-JKB76:1:1108:12602:6996 | 24048 | 24199 | 24555 | 24706 | 24048 | 24706 | | |
| M01558:36:000000000JKB76:1:2102:11483:15742 | 26512 | 26663 | 25996 | 26147 | 25996 | 26663 | 667 | 129 |
| M01558:36:000000000JKB76:1:2102:11483:15760 | 26512 | 26663 | 25996 | 26018 | 25996 | 26663 | | |
| M01558:36:000000000JKB76:1:1111:28200:12740 | 23002 | 23153 | 22438 | 22488 | 22438 | 23153 | 715 | 80 |
| M01558:36:000000000-JKB76:1:2110:2145:15071 | 23002 | 23153 | 22438 | 22568 | 22438 | 23153 | | |
| M06418:150:000000000JLVNG:1:2109:8766:27278 | 10796 | 10947 | 11491 | 11529 | 10796 | 11529 | 733 | 98 |
| M06418:150:000000000JLVNG:1:2109:8751:27286 | 10796 | 10947 | 11393 | 11529 | 10796 | 11529 | | |
| M06418:138:000000000JK9FJ:1:1111:13280:20064 | 18992 | 19143 | 19634 | 19779 | 18992 | 19779 | 787 | 94 |
| M06418:138:000000000JK9FJ:1:1111:13315:20073 | 18992 | 19143 | 19728 | 19779 | 18992 | 19779 | | |
| M06418:138:000000000-JK9FJ:1:2101:5574:6168 | 8624 | 8775 | 9377 | 9435 | 8624 | 9435 | 811 | 92 |
| M06418:138:000000000-JK9FJ:1:2101:5557:6183 | 8624 | 8775 | 9285 | 9435 | 8624 | 9435 | | |
| M06418:138:000000000-JK9FJ:1:2107:9978:11654 | 26022 | 26173 | 26833 | 26886 | 26022 | 26886 | 864 | 92 |
| M06418:138:000000000-JK9FJ:1:2107:9981:11678 | 26022 | 26173 | 26741 | 26886 | 26022 | 26886 | | |
| M06418:138:000000000JK9FJ:1:2107:20696:11842 | 14090 | 14240 | 13317 | 13348 | 13317 | 14240 | 923 | 119 |
| M06418:138:000000000JK9FJ:1:2107:20684:11863 | 14090 | 14240 | 13317 | 13467 | 13317 | 14240 | | |
| M01558:36:000000000-JKB76:1:2111:7437:17774 | 21096 | 21247 | 22122 | 22205 | 21096 | 22205 | 1109 | 68 |
| M01558:36:000000000-JKB76:1:2111:7428:17792 | 21096 | 21247 | 22054 | 22205 | 21096 | 22205 | | |

A

B

A.

Chromosome 7

B.

Translocation

C.

NEXT GENERATION SEQUENCING

This application is a Continuation of pending International Application No. PCT/US2021/055477 filed on Oct. 18, 2021, which claims priority under 35 U.S.C. § 119 on Patent Application No. 63/093,602 filed in the United States on Oct. 19, 2020, the entire contents of each of which are hereby incorporated by reference.

INCORPORATION OF SEQUENCE LISTING

The content of the electronically submitted sequence listing in the ST.26.xml file (2022-12-02_Sequence_ Listing_ST26 7072-0101PUS1.xml) filed with the application is hereby incorporated by reference in its entirety.

FIELD OF THE INVENTION

The disclosure herein pertains to methods for preparing libraries for next-generation sequencing using genomic DNA, cDNA, and/or RNA.

BACKGROUND

One of the core objectives in genetic research is to identify the variations in genomic sequence that play a role in disease development. Much progress has been made towards this goal over the last fifteen years due to improvements in sequencing technology. In particular, next-generation sequencing (NGS) technologies using DNA, RNA, or methylation sequencing have significantly reduced the time required for generating a genome sequence, as well as the cost, and holds the potential of moving personalized medicine closer to a reality.

Nevertheless, much of the genome for complex organisms remains undefined. To date, only approximately 20% of identified human protein-coding genes have an established association with one or more disease traits (Posey (2019) Orphanet Journal of Rare Diseases 14:153) while the number in other complex species is typically significantly lower. And mutations in non-coding sequence can also cause disease (McCarthy and MacArthur (2017) Genome Biol 18:20).

In addition, some less complex organisms similarly present difficulties. For example, identification of microorganisms in the gut microbiome typically rely on the use of 16S rDNA sequences (Johnson et al. (2019) Nature Communications 10:5029). While the 16S rDNA gene is relatively small (~1500-1600 bp) the high degree of conservation in sequences from different organisms, homopolymer runs, and the historical focus on the short variable sub-regions have allowed differentiation of some species, sub-species, and/or variants, many erroneous identifications have been made and copy variants missed. Without accurate determination of a particular species and its prevalence in the gut, imbalances in the gut microbiome are not diagnosed and are not properly treated. Microbiomes are becoming increasingly important in clinic. Clinical microbiomes could reveal disease interactions and the roles microbiota play in diagnosis, prognosis, and treatment of diseases and infections (Lynch et al. (2019) Nature Reviews Gastroenterology & Hepatology 16:656-661).

Similarly, without the ability to generate a complete genomic sequence from a single gene, a sample and/or a single cell, genetic diseases such as cancer, Mendelian conditions, and/or non-Mendelian conditions are difficult to diagnose and therefore to treat effectively. This is due, at least in part to complex modes of inheritance and expression, such as digenic inheritance, the presence of rare variants at two unlinked loci, incomplete penetrance, etc. In addition, most common debilitating diseases result from mutations that have occurred in many genes which individually have very small effects, yet when taken together result in disease (Gladstone Institutes (2019) "Combination of three gene mutations results in deadly human heart disease: Research study first to show multiple genes working together to cause disease" ScienceDaily 30 May 2019; Ghosh et al. (2018) Critical Reviews in Biotechnology 38 (8): 1157-1175; Raszek et al. (2016) Frontiers in Genetics 7: Article 30; Hu et al. (2018) Agriculture 8:75).

The advent of NGS has allowed significant advances in understanding the organization of genomes, the effect of variant alleles as well as the effect of copy number variants (Markham et al. (2019) Sci Rep 9:6426; Park et al. (2019) Sci Rep 9:3644; Kishore and Petrek (2018) Front. Genet. 9:503; Boutigny et al. (2019) Sci Rep 9:2308). This has led to a better understanding of gene interactions and has also provided opportunities for improved agricultural breeding for desired traits. In humans, these advances have provided new insight into allele and copy number effects on cancerous conditions.

NGS data is now also being used for virtual/molecular karyotyping to detect chromosomal abnormalities, another source of disease/disorders. Recent publications report detecting triosomy (Xu et al. (2020) Medicine 99:5), deletions or additions of chromosome parts in acute myeloid leukenia (Mack et al. (2019) Haematologica 104:277-287), and structural aberrations in pediatric acute lymphoblastic leukemia (Nordlund et al. (2020) Sci Rep 10:2512).

While NGS has come a long way, challenges remain. For example, for those companies dominating the NGS market, the vast majority of sequencing data comes from relatively short reads of up to 600 bp, but more typically about 350 bp or less. This approach has some advantages, such as for detecting single-nucleotide polymorphisms in genomic DNA and counting RNA transcripts. Problems arise, however, when reading the sequence of highly repetitive regions, extreme guanine-cytosine content, or sequences with multiple homologous elements within the genome. For example, Liao et al. (Quantitative Biology (2019) 7 (2): 90-109) list four major challenges for de novo genome assembly using NGS short reads: (1) sequence errors which introduce artifacts in the assembly results, (2) sequencing bias resulting in uneven sequencing depth across the genome, (3) topological complexity of repetitive regions causing mis arrangements, gaps, and/or uneven depth of sequencing data, and (4) computation resource consumption which can take days to weeks and over tens to hundreds of GB of peak RAM memory for large/complex genomes. Sohn and Nam (Briefings in Bioinformatics (2018) 19(1): bbw096; see FIG. 1) also highlight that after several rounds of gap filling, hundreds of gaps still remain in the genomic sequence. In addition, the data analysis is highly dependent on reference genomes which are known to be imperfect (Mantere et al. (2019) Front. Genet. 10:426). Moreover, even using reference genomes, as reported by Alkan et al. (Nat. Methods (20110) 8(1): 61-65), de novo assemblies were 16.2% shorter than the reference genome and that 420.2 megabase pairs of common repeats and 99.1% of validated duplicated sequences were missing from the genome, resulting in over 2,377 coding exons completely missing from the assembled sequence.

Some NGS long read technologies do exist. However, these also have problems. For example, DNA isolation and handling protocols for ultra-long high molecular weight DNA are cumbersome, making robust library preparation difficult. In addition, there is a higher error rate in NGS long read technology compared to NGS short read technology and reference genomes are largely still relied upon. Importantly, the cost associated with generating an NGS long read genome sequence is significantly higher.

There remains a need for robust NGS library preparations that provide longer reads than what is currently available with NGS short read technology, that can be easily organized to generate the sequence of the genome, and that does not require a reference sequence.

SUMMARY

Provided herein are robust methods, compositions, and kits for genome or gene expression analysis via long read next-generation sequencing (NGS) technology. Here, sequence reads of 2 kb or longer overcome many of the limitations associated with NGS short read technology.

At least in part, the disclosure herein is based on the development of generating populations of nucleic acid molecules, ranging in size from about 2 kb to about 50 kb and having the same distinct unique molecular identifier (UMI) located at each end of a linear nucleic acid molecule. These populations of nucleic acid molecules improve the length of NGS sequence reads, generate unbiased sequence information, and permit de novo assembly of the sequence of a genome.

In certain aspects, each nucleic acid molecule in the population is a linear nucleic acid molecule comprising, in 5' to 3' order, (a) a genomic DNA (gDNA), cDNA, or RNA molecule, (b) at least one dU nucleotide, (c) a distinct unique molecular identifier (UMI), and (d) at least one dU nucleotide, such that the population of nucleic acid molecules comprises multiple distinct UMIs.

In certain aspects, each nucleic acid molecule in the population is a circular nucleic acid molecule comprising, in 5' to 3' order, (a) a genomic DNA (gDNA), cDNA, or RNA molecule, (b) at least one dU nucleotide, (c) a distinct unique molecular identifier (UMI), and (d) at least one dU base, such that the population of circular nucleic acid molecules comprises multiple distinct UMIs, each circular nucleic acid molecule containing a distinct UMI.

In certain aspects, each nucleic acid molecule in the population is a linear nucleic acid molecule comprising, in 5' to 3' order, (a) a distinct unique molecular identifier (UMI), (b) a genomic DNA (gDNA), cDNA, or RNA molecule, and (c) the same distinct UMI as in (a), such that the population of nucleic acid molecules comprises multiple distinct UMIs.

In certain aspects, each nucleic acid molecule in the population is a linear nucleic acid molecule comprising, in 5' to 3' order, (a) a sequence primer identifier, (b) a molecular index, (c) a distinct unique molecular identifier (UMI), (d) a genomic DNA (gDNA), cDNA, or RNA molecule, (e) the same distinct UMI as in (c), (f) a molecular index, and (g) a sequence primer identifier, such that the population of nucleic acid molecules comprises multiple distinct UMIs.

In certain aspects, each nucleic acid molecule in the population is a linear nucleic acid molecule comprising, in 5' to 3' order, (a) a first sequence primer identifier, (b) a first molecular index, (c) a distinct unique molecular identifier (UMI), (d) a genomic DNA (gDNA), cDNA, or RNA molecule, (e) the same distinct UMI as in (c), (f) a second molecular index, and (g) a second sequence primer identifier, such that the population of nucleic acid molecules comprises multiple distinct UMIs.

In certain aspects, provided herein is a method of generating a population of nucleic acid molecules that can serve as sequencing templates comprising fragmenting linear nucleic acid molecules, each having a different, distinct UMI located at each end, and incubating the resulting fragments under conditions that generate a population of nucleic acid molecules where each nucleic acid molecule has the same distinct unique molecular identifier (UMI) located at each end, such that the population of nucleic acid molecules comprises multiple distinct UMIs.

In certain aspects, provided herein is method of generating a population of nucleic acid molecules that can serve as sequencing templates comprising fragmenting linear nucleic acid molecules, each having a different, distinct UMI located at each end, and incubating the resulting fragments under conditions that generate a population of nucleic acid molecules where each nucleic acid molecule has the same distinct unique molecular identifier (UMI) located central to the fragment, such that the population of nucleic acid molecules comprises multiple distinct UMIs.

In certain aspects, provided herein is a method for generating a genomic map of an organism without reliance on a reference sequence comprising preparing a population of nucleic acid molecules to serve as sequencing templates where each nucleic acid molecule has the same distinct unique molecular identifier (UMI) located at each end, such that the population of nucleic acid molecules comprises multiple distinct UMIs, conducting PCR on the population of sequencing templates using a known sequencing primer and a random N primer, conducting NGS sequencing, and aligning the nucleic acid sequences using the UMI sequences as starting points for building a genomic map.

Whether generating a de novo genomic map or a reference sequence, this approach eliminates the four limitations of NGS short read technology. Specifically, this long read methodology eliminates sequence errors which primarily occur at the ends of the sequence. Here, the multiple overlapping long reads provide only one correct nucleotide at each position. Repetitive regions of the human genome up to 700 bp in length can be covered by a single 2 kb or longer read. Hence, less computation power/resources are required to assemble a contig due to a larger overlap and identification of sequences that belong to the same long DNA read. Furthermore, gap filling is based on empirical data/sequences rather than bioinformatics software and assumptions made by the software developers.

In certain aspects, provided herein is a method for identifying indels, variants, copy number variations (CNV), translocations or chromosomal rearrangements by conducting NGS sequencing on a population of linear nucleic acid molecules where each linear nucleic acid molecule has the same distinct unique molecular identifier (UMI) located at each end, such that the population of nucleic acid molecules comprises multiple distinct UMIs, and comparing the resulting sequences to a reference genome.

In certain aspects, provided herein is a method for creating a virtual karyotype of a cell by conducting NGS sequencing on a population of linear nucleic acid molecules where each linear nucleic acid molecule has the same distinct unique molecular identifier (UMI) located at each end, such that the population of nucleic acid molecules comprises multiple distinct UMIs. No reference genome is needed here because the distinct UMI associated with each end of the population of nucleic acid molecules in conjunction with the longer sequence reads of up to 2 kb or longer allows accurate contig assembly to create a virtual karyotype for each chromosome. This aspect of the invention addresses the inability of short read NGS sequencing to detect chromosomal inversions/translocations and identify the exact fusion site and fusion sequence.

In certain aspects, provided herein is a method for determining the clonality of a sample to determine the number of cell lines present by conducting NGS sequencing on a population of linear nucleic acid molecules where each linear nucleic acid molecule has the same distinct unique molecular identifier (UMI) located at each end, such that the population of nucleic acid molecules comprises multiple distinct UMIs. No reference genome is needed because the distinct UMI associated with each end of the population of linear nucleic acid molecules in conjunction with the longer sequence reads of up to 2 kb or longer allows accurate assembly of genomic contigs. The identification of two or more types of chromosomal structural abnormalities, such as deletion, duplication, translocation, or inversion, along with the presence of normal chromosomal arrangement(s) allows estimation of the number of abnormal clones/cell lines present in a sample.

In certain aspects, provided herein is a method for generating a population of 16S rDNA nucleic acid molecules, where each nucleic acid molecule in the population is a linear nucleic acid molecule comprising, in 5' to 3' order, (a) an ILLUMINA® primer and sequencing adapter, (b) a distinct unique molecular identifier (UMI), (c) a 16S rDNA primer, and (d) a 16S RDNA sequence, such that the population of nucleic acid molecules comprises multiple distinct UMIs In certain aspects, kits containing reagents and instructions are disclosed for generating a population of linear nucleic acid molecules where each linear nucleic acid molecule has the same distinct unique molecular identifier (UMI) located at each end, such that the population of nucleic acid molecules comprises multiple distinct UMIs.

DETAILED DESCRIPTION

Definitions

Figure 1:
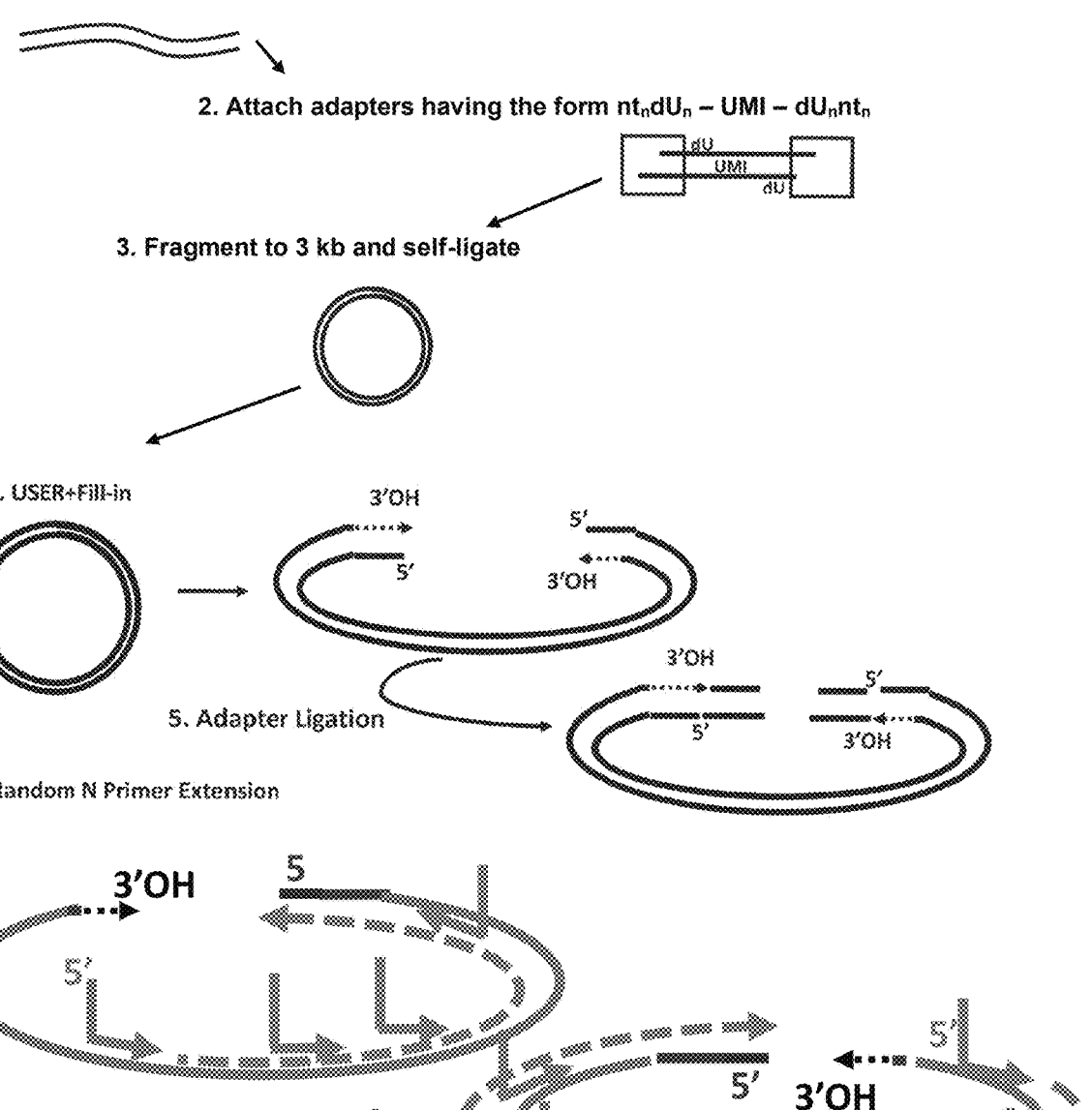
FIG. 1—Flowchart for generating a linear nucleic acid molecule having the same UMI at each end using genomic DNA (gDNA), cDNA, or RNA, overlapping fragments to form a library suitable for amplification with random N primer extension for de novo assembly of genome sequence prior to NGS. Solid lines represent a single strand of gDNA cDNA, or RNA; dotted lines represent newly replicated DNA, right-angled arrow represents random N sequencing primer; "nt" refers to nucleotide, "n" refers to a whole number greater than 0, such as 1-40, 4-30, 6-20, and all integers there between; "dU" refers to deoxyuridine; "UMI" refers to unique molecular identifier; "USER enzyme" refers to Uracil-Specific Excision Reagent; "PCR" refers to Polymerase Chain Reaction; "NGS" refers to Next Generation Sequencing.

Unless defined otherwise, all technical and scientific terms used herein generally have the same meaning as commonly understood by one of ordinary skill in the art to which this disclosure belongs. Techniques and procedures that are common in the field of molecular genetics and nucleic acid chemistry are generally performed according to conventional methods and can be found in various general references and/or laboratory manuals, such as Sambrook et al. (1989) Molecular Cloning: A Laboratory Manual, second edition, Cold Spring Harbor Laboratory Press, Cold Spring Harbor, N.Y. (which is incorporated herein by reference).

"Adapter," as used herein refers to a short, chemically synthesized, single-stranded or double-stranded oligonucleotide that can be ligated to the ends of a DNA, cDNA, or RNA molecule.

As used herein, "amplification reaction" refers to any in vitro means for multiplying one or more copies of a target sequence of nucleic acid in a linear or exponential manner. Examples of amplification reactions are polymerase chain reaction (PCR), DNA ligase chain reaction (U.S. Pat. Nos. 4,683,195 and 4,683,202), QBeta RNA replicase and RNA transcription-based amplification reactions involving T7, T3, or SP6 primed RNA polymerization, transcription amplification system (TAS), nucleic acid sequence based amplification (NASBA), isothermal amplification reactions, etc.

The articles "a" and "an" are used herein to refer to one or more than one (i.e. to at least one) of the grammatical object of the article. For example, "an element" means one element or more than one element.

As used herein, "amplifying" refers to a step of submitting a reaction solution to conditions permitting amplification of a polynucleotide. Components of the reaction solution include, for example, primers, a polynucleotide template, polymerase, nucleotides, and other needed reagents. Amplifying can result in a linear or an exponential increase in the target polynucleotide.

As used herein, two nucleic acid sequences "complement" one another or are "complementary" to one another if the base pair one another at each position.

As used herein, the term "contig" is an abbreviation for the term "contiguous" and refers to as set of overlapping DNA segments derived from a single source of genetic material that together represent a defined region of the genome from which they were derived and which provide the complete DNA sequence for that region. In bottom-up sequencing projects, a contig refers to overlapping sequence data (reads); in top-down sequencing projects contig refers to the overlapping clones that form a physical map of the genome.

As used herein, the phrase "contig map" refers to a map depicting the relative order of a linked library of small overlapping clones representing a complete chromosome segment.

As used herein, two nucleic acid sequences "correspond" to one another if they are both complementary to the same nucleic acid sequence.

"Hybridization" or "hybridizes," as used herein, refers to the act or process of forming a double stranded nucleic acid molecule from two polynucleotides that are relatively complementary to one another. In some cases, hybridization can occur between two polynucleotides that have less than 100% complementarity.

As used herein, "molecular index" or "index" refers to a short sequence tag that is ligated to all polynucleotides originating from the same sample. Molecular indices are typically at least 4 nucleotides in length, such as at least 6, 8, 10, or 12 nucleotides in length. The length of the molecular index determines how many unique samples can be differentiated. For example, a 1 nucleotide index can differentiate at most 4 different samples, a 4 nucleotide index can differentiate at most 44 or 256 samples, a 6 nucleotide index can differentiate at most 4096 different samples, and an 8 nucleotide index can differentiate at most 65,536 different samples.

As used herein, "nucleic acid" and "nucleic acid molecule" are used interchangeably and mean a polymeric form of nucleotides of any length that are DNA, cDNA, or RNA in single-stranded, double-stranded, linear, and/or circular form. The terms "nucleic acid" and "polynucleotide" are also used interchangeably herein. Non-limiting examples of polynucleotides are coding or non-coding regions of a gene or gene fragment, a locus or loci defined from linkage analysis, exons, introns, messenger RNA (mRNA), transfer RNA (tRNA), ribosomal RNA (rRNA), ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. A polynucleotide may be modified, such as by conjugation with a labeling component or interrupted by non-nucleotide components.

"Nucleotide," as used herein, is a molecule containing a nitrogenous base, a five-carbon sugar, and a phosphate group and are typically referred to by the name of their nitrogenous base: Adenine, Cytosine, Guanine, Thiamine, and Uracil. Nucleotides can be naturally occurring or can be modified. Modifications include, but are not limited to, those providing chemical groups that incorporate additional charge, polarizability, hydrogen bonding, electrostatic interaction, and points of attachment. Examples of modifications are phosphodiester group modifications (e.g. replacement with phosphonate or alkylphosphotriesters; Durand et al. (1989) Nuc Acid Res), pentose sugar modifications (e.g. dideoxynucleotide triphosphates; Sanger et al. (1977) PNAS 74 (12): 5463-5467) purine and pyrimidine modifications (e.g. cross-coupling reactions; Liang and Wnuk (2015) 20 (3): 4874-4901), base-paring alterations (e.g. isobases; Chawla et al. (2015) Nuc Acid Res 43 (14): 6714-6729), and peptide nucleic acids (see Menchise et al. (2003) PNAS 100 (21): 12021-12026). Modifications can also include addition of a fluorophore or other moieties.

As used herein, "oligonucleotide" refers to a polynucleotide that contains a relatively small number of nucleotides; that is, a polynucleotide having a short length. For example, the length of the oligonucleotide can be at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 nucleotides. Oligonucleotides are typically referred to by their length, followed by "-mer," such as hexamer, 12-mer, 25-mer, etc.

"Polymerase" refers to an enzyme that performs template-directed synthesis of polynucleotides and encompasses both the full length polymerase polypeptide and a fragment of the polymerase polypeptide containing a domain having polymerase activity. Examples of DNA polymerases include those isolated or derived from *Thermus flavus, Thermus aquaticus, Pyrococcus woesei, Thermus ubiquitous, Thermus thermophilus, Thermus litoralis*, and *Thermotoga maritima*, among others. Examples of RNA polymerases include those isolated or derived from T3 bacteriophage, T7 bacteriophage, SP6 bacteriophage, among others.

As used herein, "polymerase chain reaction" and "PCR" refer to a method of amplifying a target nucleic acid sequence in a geometric progression. PCR is well known in the art and, for DNA molecules, typically comprise either two step cycles (having a denaturation step followed by a hybridization/elongation step) or three step cycles (having a denaturation step followed by a hybridization step followed by an elongation step). For RNA PCR, the RNA is first transcribed into cDNA by reverse transcriptase and the cDNA is then used as the template for the PCR reaction.

"Primer," as used herein, refers to a polynucleotide sequence that hybridizes to a sequence on a target nucleic acid molecule and serves as a point of initiation of nucleic acid synthesis. Primers can be any length, but are typically less than 50 nucleotides in length, such as 10-30 nucleotides. Primers can be designed to complement a known sequence or can be a random sequence of nucleotides, typically known as N-random primers. In some cases, primers can include one or more modified or non-naturally occurring nucleotides.

"Reference genome," as used herein refers to a digital nucleic acid sequence database that has been assembled as a representative example of the set of genes in one idealized individual organism of a species. Reference genomes are typically assembled from a number of individual donors and do not accurately represent the set of genes of any single individual organism. Reference genomes are used as a guide on which new genomes are built.

As used herein, "sequence read" refers to an inferred sequence of nucleotides corresponding to all or part of a single polynucleotide fragment. "Read length" is the number of nucleotides sequenced and the sequence read can begin at any point along the length of the target polynucleotide fragment.

"Sequencing depth" and "read depth" are used interchangeably and describe the number of times that a given nucleotide in the sample population has been read in an experiment. The individual reads are bioinformatically overlapped or "tiled" to generate longer contiguous sequences that can make up meaningful data/increased accuracy for an RNA population or genomic sequence.

A "template," as used herein refers to a polynucleotide sequence that comprises the polynucleotide to be amplified, flanked by at least one primer hybridization site. In some cases, a target template comprises the target polynucleotide sequence flanked by a hybridization site for a "forward" primer and a "reverse" primer.

As used herein, "Tm" refers to the melting temperature of two polynucleotides at which 50% of the polynucleotides are bound and 50% of the oligonucleotide molecules are not bound.

"UMI," as used herein, refers to a unique molecular identifier that can be attached to at least one end on a polynucleotide and acts as a molecular tag that allows identification of the polynucleotide to which it is attached in a population of polynucleotides having different UMIs.

As used herein, "USER" and "USER enzyme" refers to uracil-specific excision reagent which cleaves at a deoxyuracil (dU), creating a single nucleotide gap at each location of dU and resulting in a polynucleotide fragment flanked with at least one single-stranded extension that allows seamless and directional assembly of customized molecules.

DISCLOSURE

One aspect of the disclosure provided herein is a method of NGS library production as shown in FIG. 1. Here, in Step 1, genomic DNA (gDNA), cDNA, or RNA is isolated. This can be accomplished using a method presented in a laboratory manual, such as Sambrook et al. (1989) Molecular Cloning: A Laboratory Manual, or by using a commercially available kit, such as those available from Thermo Fisher Scientific (Carlsbad, CA), Bio-Rad (Hercules, CA), Qiagen (Germantown, MD), Promega (Madison, WI), Zymo Research (Irvine, CA), Agilent (La Jolla, CA), or Roche Life Science (Penzberg, Germany), to name but a few.

Next, the isolated gDNA, cDNA, or RNA is fragmented. If RNA is the starting material, because of its size no fragmentation is needed, although RNA nucleic acids are first converted to cDNA using methods standard in the art. When needed, fragmentation can be accomplished by sonication, treatment with dsDNA FRAGMENTASE® (available from NEB, Ipswich, MA), restriction enzyme treatment, manual shearing, etc. Suitable sonicator devices are commercially available from COVARIS® (Woburn, MA), Diagenode (Denville, NJ), Qsonica (Newtown, CT), Fisher Scientific (Carlsbad, CA), Thomas Scientific (Swedesboro, NJ), and PRO Scientific (Oxford, CT), to name but a few. Restriction enzymes are widely available from laboratory reagent supply stores, such as NEB (Ipswich, MA), Promega (Madison, WI), Thermo Fisher Scientific (Carlsbad, CA), Bio-Rad (Hercules, CA), Zymo Research (Irvine, CA), and Promega (Madison, WI), to name but a few. Fragments resulting from treatment with restriction enzyme that cleave asymmetrically, leaving single stranded overhangs ("sticky ends"), are ready for Step 2. However, when fragmentation is conducted via a method other than treatment with asymmetrically cleaving restriction enzymes, the polynucleotide fragments must be submitted to end-repair and/or A-tailing. Protocols for end-repair and A-tailing are widely available, such as in Sambrook et al. (1989) Molecular Cloning: A Laboratory Manual, and kits to accomplish these treatments are also available, for example from NEB (Ipswich, MA), Roche (South San Francisco, CA), and Thermo Fisher Scientific (Carlsbad, CA).

The fragmentation results in polynucleotide fragments having an average size in the range of about 2 kb to about 50 kb, such as an average size of at least 2 kb, 3 kb, 4 kb, 5 kb, 6 kb, 7 kb, 8 kb, 9 kb, 10 kb, 11 kb, 12 kb, 13 kb, 14 kb, 15 kb, 20 kb, 25 kb, 30 kb, 35 kb, 40 kb, or 50 kb.

Once the polynucleotide fragments having single strand overhangs are generated, adapters are attached via ligation to each end of the polynucleotide fragment. The population of polynucleotides is combined with a population of double stranded adapters, each adapter comprising, in 5' to 3' order, (a) a short oligonucleotide containing at least one dU nucleotide, (b) a unique UMI, and (c) either a restriction enzyme overhang compatible with the restriction enzyme overhang generated in Step 1 via fragmentation or a T overhang compatible with the A-tail present on the fragment.

In this step, each end of the polynucleotide fragments has a different unique UMI. Examples of suitable adapters are NEBNEXT® adapters (NEB, Ipswich, MA) and Roche KAPA adapters (South San Francisco, CA). Such dU containing oligonucleotides can be synthesized by companies such as Synbio Technologies (Monmouth Junction, NJ) and then, if needed, attached to a collection of unique UMIs having either sticky ends or T-tails. Alternatively, custom adaptors containing (a)-(c) are synthesized together generating a collection of unique UMIs such that no attachment is needed, for example by Integrated DNA Technologies (Coralville, IA). The resulting adapter-polynucleotide-adapter molecules have blunt ends or have a T overhang to be ligated to the A overhang produced after fragmentation and repair of the nucleic acids. In some cases the UMI sequence contains a variable number of random nucleotides (i.e., "N," any one of which can be A, C, G, T, or U or modifications thereof), such as 1-40, 4-30, 6-20. As an example, the UMI may have the sequence shown in FIG. 3 with 11 random nucleotides:

$$\text{(SEQ ID NO: 1)}$$
$$\text{5'P-UCUNNNNNNNNNNNNACAT-3'OH}$$

$$\text{(SEQ ID NO: 2)}$$
$$\text{OH 3'-TAGANNNNNNNNNNNNUGU-5'P}$$

After attachment of the adaptors, Step 3 is performed. Here, a second fragmentation is performed, this time using the polynucleotides generated in Step 2 which have adapters with unique UMIs. Any of the fragmentation procedures discussed above can be used. If fragmentation occurs by sonication/shearing/dsDNA Fragmentase, blunt ends are ensured by repairing using standard methods. If fragmentation occurs via cleavage with an asymmetric enzyme, one or more is selected that has sticky ends that will allow ligation to those present on the adapter. In some instances, the fragmented polynucleotides having adapters with unique UMIs are isolated and in other instances no further isolation is conducted.

The sample containing the fragmented polynucleotides having adapters with unique UMIs is then diluted to prevent hetero-concatemer formation and the polynucleotides are self-ligated/circularized. Linear DNA remaining in the self-ligation reaction is removed using exonuclease, such as exonuclease V, exonuclease VI, etc. Each self-ligated, circular polynucleotide has one of the two adapters having unique UMIs that were attached in Step 2.

Step 4 involves USER enzyme treatment of the self-ligated, circular polynucleotide. Here, the USER enzyme creates a single nucleotide gap at each location of dU and generates a linear polynucleotide having one strand of the UMI attached to each end of the linear polynucleotide. End repair is then conducted resulting in a fully double stranded polynucleotide having an identical UMI at each of its ends (see FIG. 1).

Importantly, because the adapters added in Step 2 represent a population containing numerous unique UMIs, the resulting collection of polynucleotides provides the ability for de novo genome assembly, virtual karyotyping, identification of indels, variants, copy number variations (CNV), translocations and/or chromosomal rearrangements.

That is, when genomic fragments were first sequenced using Sanger sequencing, de novo assembly was used for all genomes, including humans. However, short read NGS sequences can only be used for identification of a targeted fusion, which means it can only detect fusions for a certain number of genes and cannot detect any chromosomal inversions/translocations nor identify the exact fusion site and fusion sequence.

Figure 12:
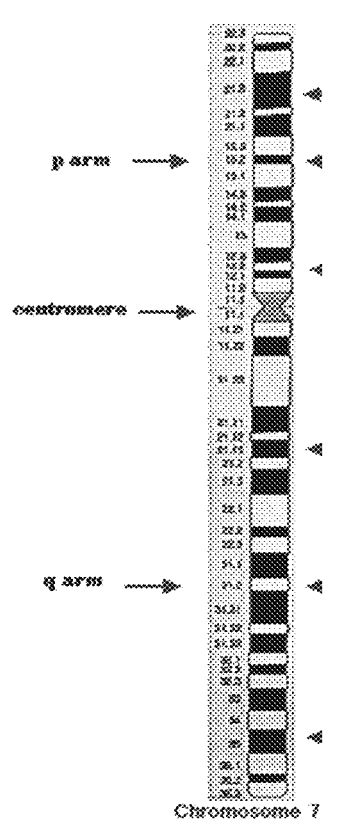
FIG. 12—Schematics of virtual karyotyping. A: Depiction of karyotyping bands assigned to a single chromosome, showing the p arm, centromere, and q arm on the left and using arrowheads on the right to identify specific karyotype bands. B: Depiction of a translocation between chromosome 4 and chromosome 20 where the translocated regions are shown within brackets. C: Depiction of a translocation between the q arm of chromosome 6 and the p arm of chromosome 7. The arrow pointing to the q arm of the chromosome identified as der(6) indicates the juncture point of the translocation with the p arm of chromosome 7 and provides the sequence at the juncture point. Similarly, the arrow pointing to the p arm of the chromosome identified as der(7) indicates the juncture point of the translocation with the q arm of chromosome 6 and provides the sequence at the juncture point.
Figure 12:
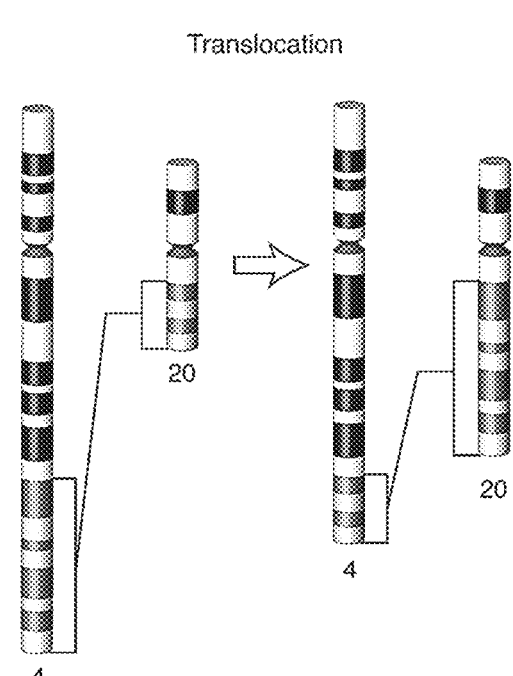
Figure 12:
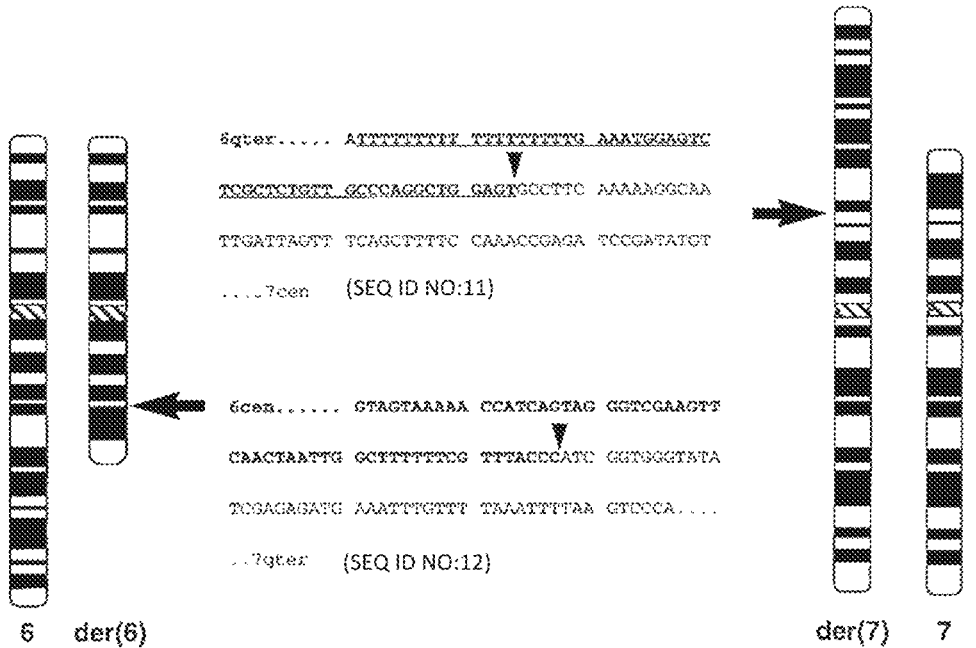

Specifically, using 2 kb or longer reads of DNA sequences generated by the disclosed methodology, DNA segments are assembled from sequences of the same DNA origin and are used to create a de novo assembly of the chromosome contigs. Each chromosome is assigned its correct number (e.g., in humans 1-22, X, or Y). This is done by comparing the sequences present in each of the assembled chromosomes to existing karyotyping banks and assigning karyotyping bands to each assembled chromosome based on its sequence (see FIG. 12A). Any discrepancy between the normal/expected banding pattern and the observed/identified banding is noted/flagged by the software. Chromosomes having bands coming from other chromosomes or being moved within the same chromosome are identified as a translocation or an inversion (see FIG. 12B). Because the sequence on each chromosome comes from a 2 kb or longer DNA segment, the software can pinpoint the fusion sequence of the translocated or inverted regions (see FIG. 12C). This is not possible using existing technologies such as the ILLUMINA® mate pair sequencing, which allows distant sequences to be identified, yet does not reliably and unequivocally identify the entire junction sequence due to the presence of gaps, especially in the repeat regions, and the reliance on a reference mandated by short read NGS.

Step 5 involves ligation of a second adapter containing a sequencing primer site and/or a sequencing primer site and molecular index to each end of the polynucleotide of Step 4 (see FIG. 1). Such adapters are available from Integrated DNA Technologies (Coralville, IA), among other companies. Each polynucleotide in the collection has, in 5' to 3' order, the following: (a) a sequencing primer site, (b) optionally a molecular index, (c) a unique UMI, (d) a polynucleotide fragment from Step 3, (e) the same unique UMI as (c), (f) optionally the molecular index of (b), and (g) a sequencing primer site. In some instances, the sequencing primer sites of (a) and (g) are identical, in other instances they are different. Suitable sequencing primer sites are those recognized by P5 and P7.

In some aspects, the resulting nucleic acid fragment contains, in 5' to 3' order, P7 sequence, a P7 end molecular index, a read 1 and/or gene specific primer site, the target nucleic acid, a read 2 primer site, read 2 sequencing primer site, a P5 end molecular index, and a P5 sequence.

The polynucleotide population generated in Step 5 is then subjected to an initial PCR amplification using primers corresponding to the sequencing primer site(s) or using a random N primer extension approach (shown in FIG. 1). Random N primer extension kits are commonly available from NEB (Ipswich, MA), Thermo Fisher Scientific (Carlsbad, CA), Stratagene (La Jolla, CA), and Agilent (Santa Clara, CA), to name but a few, and the extension conducted according to the manufacturer's directions.

Figure 2:
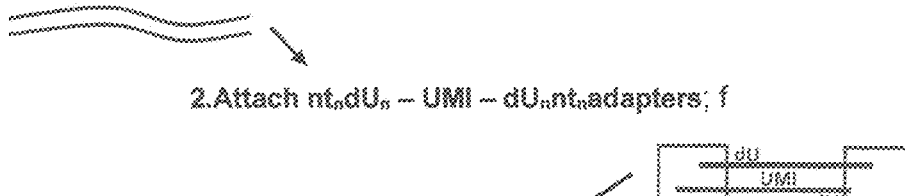
FIG. 2—Flowchart for generating a linear nucleic acid molecule having a single centrally located UMI using genomic DNA (gDNA), or cDNA for NGS library production Solid lines represent a single strand of DNA, cDNA, or RNA; "nt" refers to nucleotide, "n" refers to a whole number greater than 0, such as 1-40, 4-30, 6-20, and all integers there between; "dU" refers to deoxyuridine; "UMI" refers to unique molecular identifier; "USER enzyme" refers to Uracil-Specific Excision Reagent; "PCR" refers to Polymerase Chain Reaction; "NGS" refers to Next Generation Sequencing.
Figure 2:
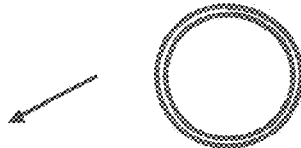
Figure 2:
Figure 2:
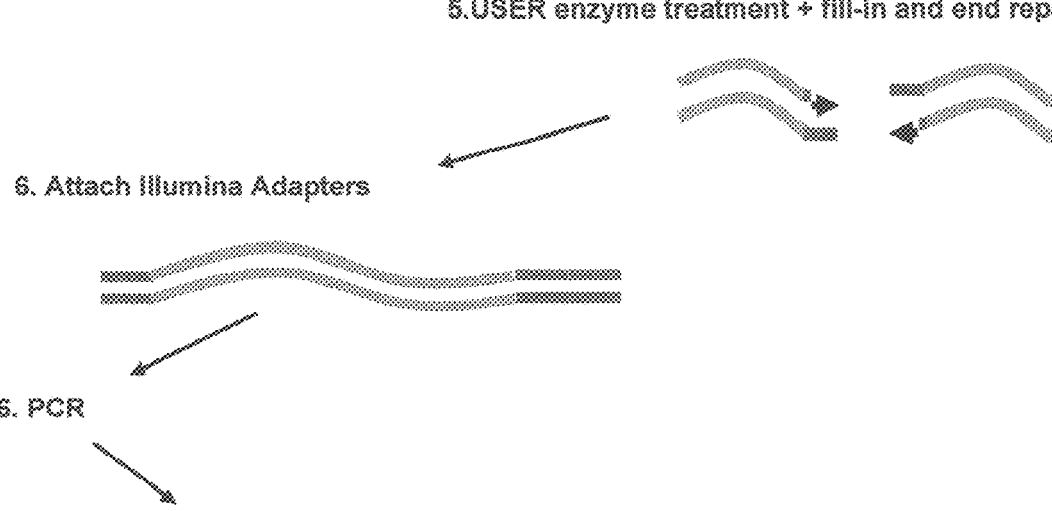

Alternatively, the procedure shown in FIG. 2 is followed. Here, after performing Steps 1-3 the self-ligated circular DNA or RNA molecule is fragmented. Any of the fragmentation procedures discussed above can be used. If fragmentation occurs by sonication/shearing/dsDNA Fragmentase, blunt ends are ensured by repairing using standard methods. If fragmentation occurs via cleavage with an asymmetric enzyme, one or more is selected that has sticky ends that will allow ligation to those present on the adapter. It only after this fragmentation that USER enzyme treatment, fill-in, and end repair/A-tailing is conducted. ILLUMINA® adapters are then attached before conducting a final PCR step.

In all cases, flow cell binding sequences are added to each resulting nucleic acid fragment prior to the final PCR step.

This completes NGS library; however, the collection is then typically subjected to a final PCR amplification to ensure sufficient representation of fragments in the library population.

Figures 3, 4:
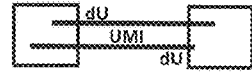
FIG. 3—Example of adapters having the form $nt_n dU_n$—UMI—$dU_n nt_n$. "nt" refers to nucleotide, "n" refers to a whole number greater than 0, such as 1-40, 4-30, 6-20, and all integers there between; "dU" refers to deoxyuridine; "UMI" refers to unique molecular identifier; "N" refers to Adenine, Guanine, Cytosine, Thymine, Uracil, or modifications thereof.
FIG. 4—Schematic of how sequencing using a fixed primer at one end and random primers annealing to various segments of the insert results in a longer DNA fragment read and how all reads come from the same DNA fragment.

Depending on the purpose for the NGS library, NGS sequencing is conducted using primers directed to known polynucleotide sequences in an organism's DNA or RNA (see FIG. 3) or is conducted using random N primer extension (see FIG. 1). When using random N primer extension, the primer contains a sequencing primer tail which does not rely on a reference sequence. Such random N primers are available from NEB (Ipswich, MA) and Thermo Fisher Scientific (Carlsbad, CA), among others. A typical sequence read from the NGS library disclosed above is at least about 1500 base pairs, which is significantly longer than what is normally achieved using standard NGS library preparations. FIG. 4 illustrates how using a fixed primer and random primers on the other end results in a longer DNA fragment and indicates that all sequences come from the same DNA fragment.

In addition, because each member has a different, unique UMI at each end of the linear polynucleotide fragment as shown in FIG. 1, when using random N primer extensions there is no need for a reference sequence. Since the initial step of the NGS library preparation was fragmentation of the starting collection of polynucleotides followed by size selection, the resulting original fragments themselves contained overlap. That fact, in combination with the second fragmentation and duplication of the UMI associated with the fragment resulting from the second fragmentation allows alignment of sequences without reliance on a reference sequence.

Figure 11:
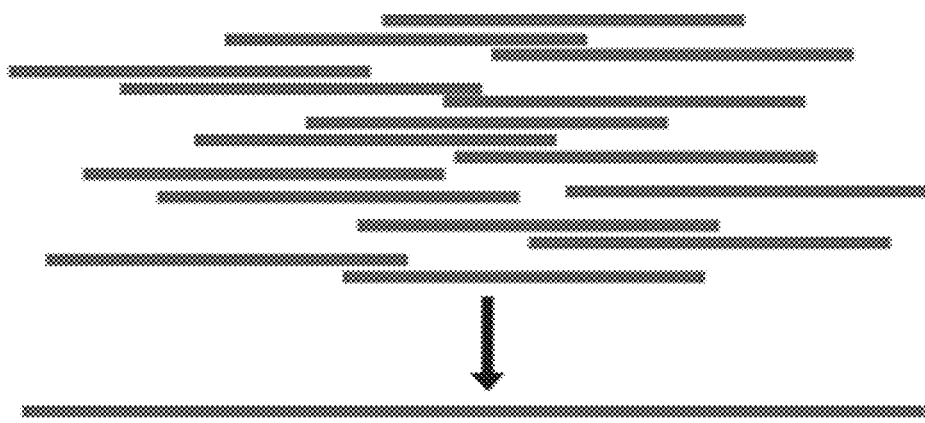
FIG. 11—Schematic showing that using DNA sequence reads of up to 2 kb or longer permits generation of a large contig and de novo genome assembly by removing the need for a reference genome alignment.

As a simplified example, consider a 3 kb polynucleotide having UMI #1 at each end. Sequencing with random N primers will generate a series of at least ~1500 bp reads from each of the two strands of DNA, each read originating at a different point in the 3 kb fragment. Similarly, a 3 kb polynucleotide having UMI #2 at each end that is sequenced with random N primers will generate a series of at least ~1500 bp reads from each of the two strands of that DNA. This then allows aligning/overlapping of the sequences using UMI #1 and UMI #2 as the starting points to generate the full sequence of the fragment having UMI #1 and the full sequence of the fragment having UMI #2. Consequently, between the sequence overlap of the original size selected polynucleotides, the overlap in the sequence reads of the final NGS library collection and the presence of UMI #1 and UMI #2 in the sequence reads, one can determine the exact 5' to 3' sequence located on the original gDNA, cDNA, RNA polynucleotide as shown in FIG. 11.

In addition to generalized genomic sequencing, the technology presented herein can be used for targeted sequencing. Here, the method uses the random UMI tagging on one end of the target sequence and a random primer extension on the other end. This allows accurate identification of the sequence, especially in situations where, for example, sequences from different organisms have high homology and/or have long runs of homopolymers and/or high G-C content.

Figure 10:
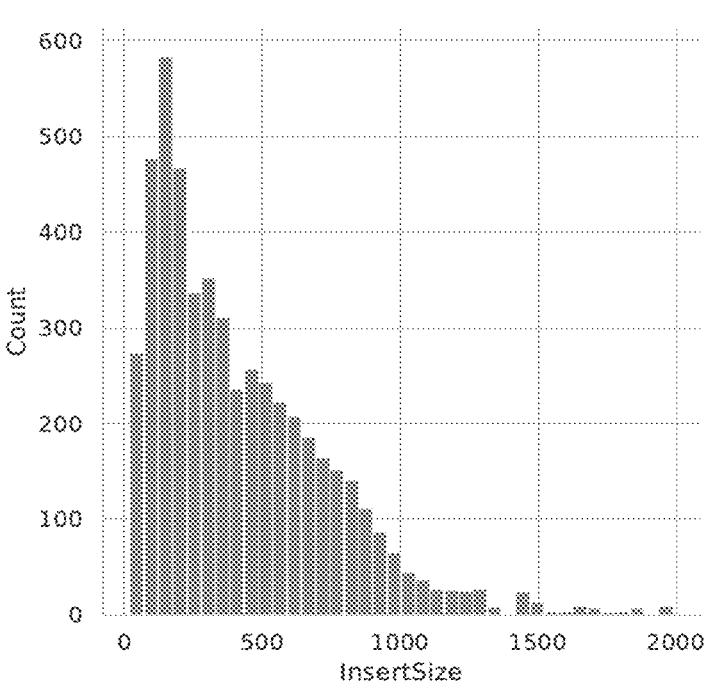
FIG. 10—Insert size distribution based on sequencing results for two different libraries showing inserts of up to 2 kb. A: Library F4S; B: Library F4L.
Figure 10:
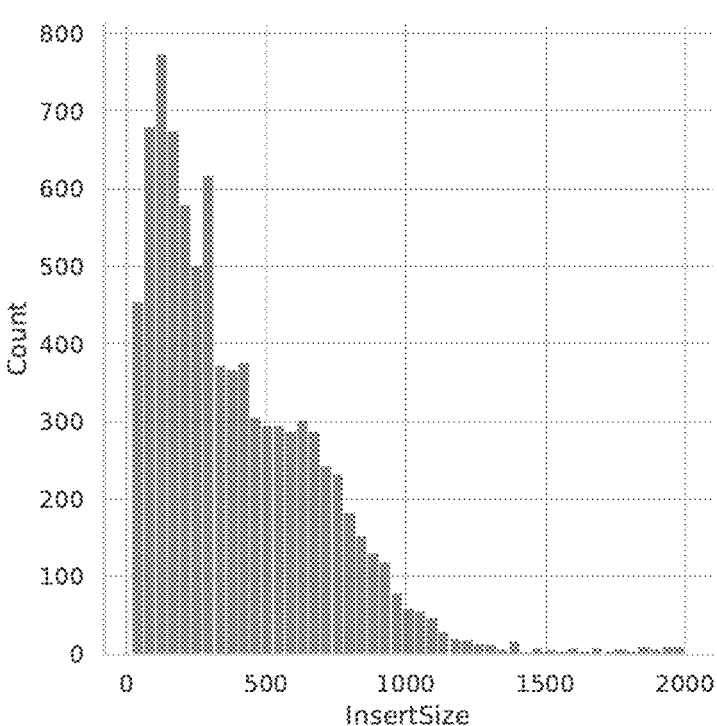
Figure 13:
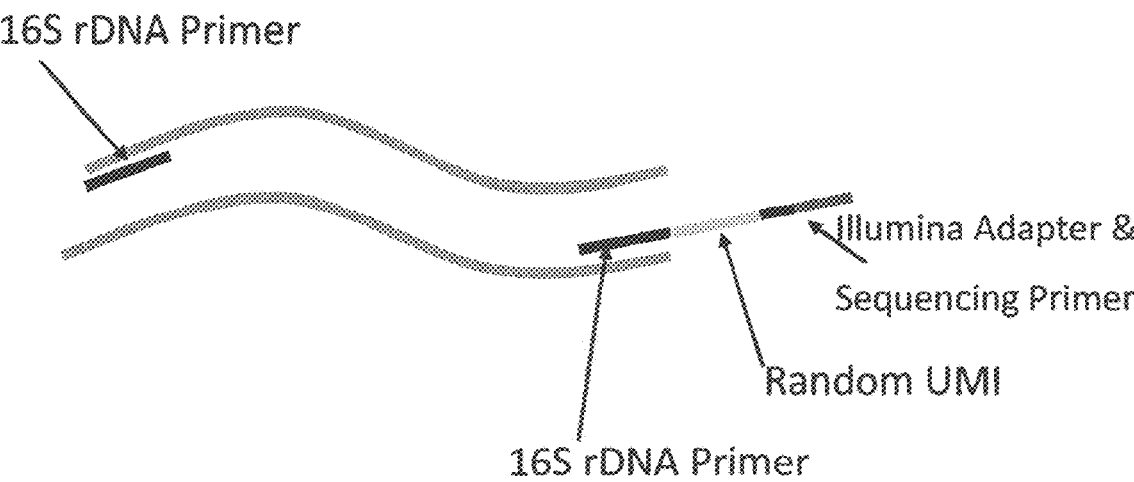
FIG. 13—Schematic showing PCR amplification of 16S rDNA where a 16S rDNA reverse primer is used at one end of the 16S rDNA nucleic acid and a primer comprising ILLUMINA® Adapter and Sequencing Primer joined to a random UMI joined to a 16S rDNA forward primer.
Figure 14:
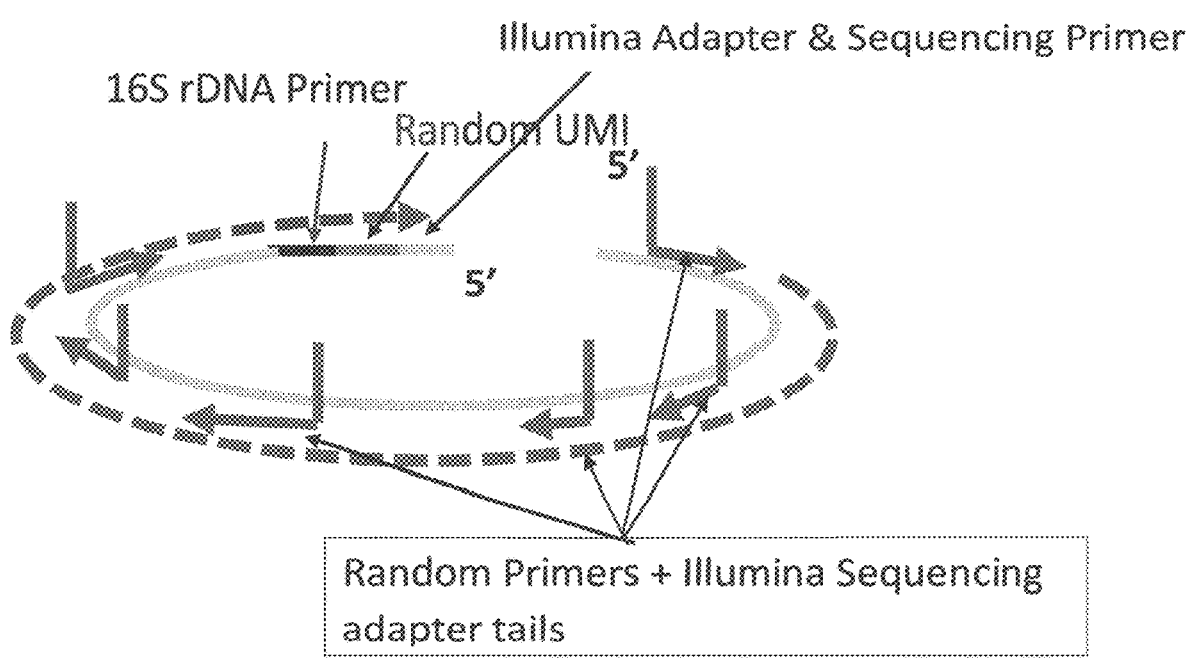
FIG. 14—Schematic of a random N primer extension of a 16S rDNA PCR product.

FIG. 13 illustrates how targeted sequence can work using bacterial 16S rDNA as an example. PCR amplification is conducted using a 16S specific primer for one end of the molecule and at the other end of the molecule a primer comprising an ILLUMINA® adapter and sequencing primer joined to a random UMI joined to a 16S rDNA specific primer. As shown in FIG. 14, the amplified products are then sequenced with random primers having sequencing adapter tails. The segments are then aligned using these features in a manner essentially identical to that shown in FIG. 4. As indicated by the size distribution shown in FIGS. 10A and B, the 16S rDNA~1500-1600 bp sequence could be completely covered.

Examples

The following examples are provided by way of illustration only and not by way of limitation. A variety on non-critical parameters can be changed or modified to yield essentially the same or similar results.

A. Library Production for De Novo Genomic Sequence Assembly (FIG. 1)

Step 1—Fragmentation

Up to 30 μg/g-TUBE (Covaris, Boston, England) of non-degraded, fully solubilized DNA in DI water or TE (10 mM Tris, 0.1 mM EDTA, pH 8.0) or 10 mM Tris-Cl, pH 8.5 having a starting size larger than 45 kbp is vortexed for 10s and pre-warmed at room temperature (20° C. to 30° C.). The sample containing g-TUBE is centrifuged for 30 seconds at 13, 300 rpm (16,276 rcf(g)) to drain the sample from the upper chamber of the g-TUBE and transfer it to the bottom of the tube. Tubes are inverted and the centrifugation step repeated using the same time and speed. Sheared DNA is recovered, reapplied to the upper chamber of the same g-TUBE, the centrifugation and inversion repeated twice, and the sheared DNA again recovered. DNA is concentrated using a Zymo DNA concentration kit (Zymo; Irvine, CA). Average size of the fragmented gDNA is measured by loading 2 μl of the sample on a 1% agarose gel. Samples having an average size of ~6 kb are selected.

Step 2—Adapter Attachment

1 μg of fragmented DNA is brought to a 50 μl volume using EB buffer (10 mM Tris-Cl, pH 8.5) prior to adding 3 μl of NEBNEXT® ULTRA™ II end prep enzyme mix (NEB, Ipswich, MA) and 7 μl of NEBNEXT® ULTRA™ II end prep reaction buffer (NEB, Ipswich, MA). Sample is incubated for 30 minutes at 20° C. followed by a 30 minute incubation at 65° C.

The molarity of the fragmented DNA is calculated according using the following values: DNA length of ~6 kb, 1 ug=0.25 pmol; dU-UMI is 18 bp at 100 uM/0.2 ug=16.83 pmols. A 10-100 molar excess of adapters are used. 2.5 μl of IDT: dU-UMI+T (Integrated DNA Technologies, Coralville, Iowa) overhang adapters are mixed with 1 μl of NEB-NEXT® ligation enhancer (NEB, Ipswich, MA) and 30 μl of NEBNEXT® ULTRA™ II Ligation master mix (NEB, Ipswich, MA) prior to incubating for 15 minutes at 20° C.

SPRI Beads Purification

SPRI beads 1:0.7×(65 μl of SPRI) are added to the sample and incubated for 5 minutes at room temperature. After placing on the magnet, the sample is further incubated another 5 minutes before adding 200 μl of 80% ethanol and incubating 30 seconds to wash. Sample is again placed on the magnet and excess ethanol removed. Sample is air dried for no more than 2 minutes, resuspended in 18 μl EB buffer (10 mM Tris-Cl, pH 8.5), incubated for 2 minutes, and again placed on the magnet to recover 16 μl. Sample can then be stored at 4° C. for up to 72 hours or at −20° C. for longer periods.

Step 3—dsDNA Fragmentase Reaction

A digestion using NEBNEXT® dsDNA Fragmentase (NEB, Ipswich, MA) is conducted by combining 5 ng-3 μg of prepared DNA in 16 μl, 2 μl of NEBNEXT® dsDNA Fragmentase reaction buffer (NEB, Ipswich, MA) and 2 μl of NEBNEXT® dsDNA Fragmentase. The reaction is incubated for 5 minutes on ice prior to a 4 minute incubation at 37° C. 5 μl of 0.5 M EDTA is added to stop the reaction and a 5 μl sample electrophoresed on a 1% agarose gel to assess fragment size. Samples having an average size of 3 kb are selected and the volume adjusted to 50 μl with water.

The digested DNA is purified using the SPRI procedure described above.

End Repair

3 μl of T4 PNK/T4 polymerase is added to the 50 μl sample of purified DNA along with 7 μl of reaction buffer (Thermo Fisher, Carlsbad, CA; NEB, Ipswich, MA) and incubated for 30 minutes at 20° C. SPRI purification is conducted essentially as set forth above, but using SPRI beads 1:0.8×(48 μl of SPRI).

Self-Circularization

50 μl of DNA, 5 μl of T4 DNA ligase high concentration (cat #M0202T; NEB, Ipswich, MA), 140 μl of T4 DNA ligase buffer (NEB, Ipswich, MA) and 460 μl of H₂O are mixed and incubated at 16° C. for 4 hours (or overnight at 4° C.) with interval shaking. The reaction is heat inactivated at 65° C. for 10 minutes.

Purification

Purification is conducted using SPRI beads 1:0.7× by mixing 710 μl of DNA, 50 μl of SPRI beads and 450 μl of buffer (20% PEG 8000 w/v, 2.5 M NaCl, 10 mM Tris-HCl, 1 mM EDTA, 0.05% Tween 20 v/v, pH 8.0). The sample is resuspended in 18 μl EB buffer (10 mM Tris-Cl, pH 8.5), incubated for 2 minutes, and again placed on the magnet to recover 16 μl.

Step 4-USER+Fill-In

2 μl of CutSmart 10× buffer (NEB, Ipswich, MA) and 2 μl of USER enzyme (NEB, Ipswich, MA) is added and the sample incubated at 37° C. for 30 minutes. 2 μl of Antarctic Phosphatase Reaction Buffer (10×) and 1 μl of Antarctic Phosphatase (NEB, Ipswich, MA) is then added and the reaction incubated for another 30 minutes at 37° C. The reaction is heat inactivated by incubating at 80° C. for 5 minutes. 3 μl of NEBNEXT® ULTRA™ II End Prep Enzyme Mix (NEB, Ipswich, MA) is then added, the sample incubated for 30 minutes at 20° C., and then incubated for 30 minutes at 65° C.

Step 5-Adapter Ligation

A ligation is performed by adding 2.5 μl of 15 uM Adapter of a fully-dsDNA adapter that has been designed as a truncated P7 adapter, for example:

```
                                      (SEQ ID NO: 3)
5'-GGGGGGACTGGAGTTCAGACGTGTGCTCTTCCGATCT-3'

(SEQ ID NO: 4)
3'-AAAAACTGACCTCAAGTCTGCACACGAGAAGGCTAG/5Phos/-5'
```

These can be ordered from IDT or ILLUMINA®. 1 μl of Enhancer and 30 μl of Ligation Mix (all from NEB, Ipswich, MA) are added to the sample. The solution is incubated for 15 minutes at 20° C. Purification is conducted using SPRI beads 1:0.9× essentially as described above. The purified sample is resuspended in 20 μl EB buffer and 18.5 μl of purified product recovered.

Step 6—Random Primer Extension

1 μl of 25 uM truncated-P5 random primer and 2.5 μl of SD polymerase 10× buffer (Boca Scientific, Dedham, MA) are added to the sample, incubated at 98° C. for 2 minutes and immediately placed on ice for 3 minutes. 2 μl of 10 mM dNTP mix and 1 μl of SD DNA Polymerase are added and the sample is subjected to several cycles of incubation for 3 minutes at 92° C.; incubation for 5 minutes at 16° C.; a 0.1° C./second ramp to 68° C.; and extension at 68° C. for 5 minutes. This produces different sized molecules from the 3 kb fragment from both ends, all ending with the random UMI associated with that fragment, as illustrated in FIG. 4, which could be 2 kb or longer. The genome map is similarly generated from each continuous sequence or contig associated with each random UMI, as illustrated in FIG. 11.

The reaction volume is increased to 50 μl with EB buffer and two rounds of SPRI-bead purification are conducted, essentially as described above, using 100 μl of SPRI-beads. The products are eluted with 22 μl of EB buffer and 20 μl of purified product obtained.

Barcoding PCR

25 μl of Q5® Hot Start High-Fidelity 2× Master Mix, 2.5 μl of Universal Primer and 2.5 μl of barcoded primer (NEBNEXT® multiplex oligo kit, Ipswich, MA) are added to 20 μl of the purified product. PCR is conducted by first incubating for 30 seconds at 98° C.; and then conducting at least 5 cycles using the following cycling times: 98° C. for 10 seconds; 65° C. for 30 seconds; 72° C. for 60 seconds. A final extension is performed for 5 minutes at 72° C. prior to holding at 4° C.

SPRI-bead purification is conducted using 1:0.9× beads essentially as described above. Elution is conducted with 17 μl EB buffer and 15-16 μl of purified product is obtained. Fragment size is assessed on a TapeStation (HS-D1000 or D5000 Assay; Agilent, San Diego, CA) and quantitated using the Qubit assay (dsDNA BR or dsDNA HS; Thermo Fisher Scientific, Carlsbad, CA).

MISEQ™ Sequencing

Sequencing was conducted using the MISEQ™ System (ILLUMINA®, San Diego, CA) according to the manufacturer's instructions. Loading concentrations were 6-20 pM for Kit v3 and 6-10 pM for Kit v2 (300 cycle kit). Samples were 4-6 ng/μl (~10 nM).

Contig Formation

The individual reads are bioinformatically overlapped to generate longer contiguous sequences or contigs where each continuous sequence or contig is associated with a specific random UMI as illustrated in FIG. 4. The genome map is similarly generated from each UMI continuous sequence or contig, as illustrated in FIG. 11.

B. Library Preparation for Genomic Sequence Assembly Using Reference Sequences (FIG. 2)

Steps 1-3 are conducted as shown above.

Linear Digestion of Self-Circularized DNA

5 μl of Thermolabile exonuclease I and 5 μl of exonuclease V (RecBCD) (NEB, Ipswich, MA; Thermo Fisher, Carlsbad, CA) is added to the self-circularized sample and incubated at 37° C. for 2 hours with interval shaking. Inactivation of the reaction is accomplished by incubating at 80° C. for 20 minutes. Purification is conducted using SPRI beads 1:0.7× by mixing 710 μl of DNA, 50 μl of SPRI beads and 450 μl of buffer (20% PEG 8000 w/v, 2.5 M NaCl, 10 mM Tris-HCl, 1 mM EDTA, 0.05% Tween 20 v/v, pH 8.0) according to the manufacturer's directions. The isolated linear DNA is resuspended in 18 μl of EB (10 mM Tris-Cl, pH 8.5) and 16 μl recovered.

Further Fragmentation

An additional/optional fragmentation step is conducted using an enzymatic method as described above or via a sonicator. If performing an enzymatic digestion, purification is required, such as using SPRI beads 1:0.7× as described above, but is not necessary for sonication, which is done in a minimum volume of 50 μl. The goal is an average size of 1 kb. After the further fragmentation procedure, DNA size is assessed on a 1.2% agarose gel.

USER Treatment, End Repair and A-Tailing

7 μl of NEBNEXT® ULTRA™ II End Prep Reaction Buffer (NEB, Ipswich, MA) and 3 μl of USER enzyme (NEB, Ipswich, MA) is added to 50 μl DNA prior to incubation at 37° C. for 30 minutes. The reaction is heat inactivated by incubation for 5 minutes at 60° C. 3 μl of NEBNEXT® ULTRA™ II End Prep Enzyme mix (NEB, Ipswich, MA) is added, incubated at 20° C. for 30 minutes and then incubated for a further 30 minutes at 65° C.

Alternatively, 7 μl of NEBNEXT® ULTRA™ II End Prep Reaction Buffer (NEB, Ipswich, MA) and 3 μl of USER enzyme (NEB, Ipswich, MA) is added to 50 μl DNA prior to incubation at 37° C. for 30 minutes. 3 μl of Klenow Fragment (3'-5' exo-; NEB, Ipswich, MA) is added to the solution and incubated for 30 minutes at 37° C. prior to the addition of 3 μl NEBNEXT® ULTRA™ II End Prep Enzyme mix (NEB, Ipswich, MA). The reaction is then incubated at 20° C. for 30 minutes and then incubated for a further 30 minutes at 65° C.

ILLUMINA® Adapter Ligation

A ligation is performed by adding 2.5 μl of 15 uM Adapter (stem loop) from NEB Next Multiplex Oligos for ILLU-MINA® along with 1 μl of Enhancer and 30 μl of Ligation Mix (all from NEB, Ipswich, MA) to the sample generated from USER treatment+End Repair and A-tailing. The solution is incubated for 15 minutes at 20° C. 3 μl of USER enzyme is then added and incubated for a further 15 minutes at 37° C. Purification is conducted using SPRI beads 1:0.85× (80 μl of SPRI) essentially as described above. The purified sample is resuspended in 25 μl EB buffer and 22.5 μl recovered. This is the sample used in the final PCR reaction.

Final PCR

If desired, sample barcodes can be introduced, such as when a truncated adapter like the NEBNEXT® Multiplex Oligos for ILLUMINA® (96 Unique Dual Index Primer Pairs (NEB, Ipswich, MA) was used during the adapter litigation. Reaction composition and reaction conditions vary depending on the DNA polymerase used, but are conducted according to the manufacturer's instructions.

PCR amplification is conducted using the following PCR cycling conditions

| Cycle Step | Temperature | Time | Cycles |
|---|---|---|---|
| Initial Denaturation | 98° C. | 30 seconds | 1 |
| Denaturation | 98° C. | 10 seconds | 3-15* |
| Annealing/Extension | 65° C. | 75 seconds | |
| Final Extension | 65° C. | 5 minutes | 1 |
| Hold | 4° C. | ∞ | |

*The number of PCR cycles is chosen based on input amount and sample type. That is, the number of cycles is high enough to provide sufficient library fragments for a successful sequencing run, yet low enough to avoid PCR artifacts and over-cycling.

The amplified sample is purified using SPRI beads 1:0.9× (45 μl of SPRI) essentially as described above. The purified sample is resuspended in 25 μl of EB and 22.5 μl recovered. For quality control purposes, the NGS library can be evaluated using Qubit concentration measurements (ThermoFisher Scientific, Carlsbad, CA), TapeStation (HS-D100 or D1000 Assay; Agilent, San Diego, CA) or, optionally, qPCR for a more accurate quantification.

MISEQ™ Sequencing

Sequencing was conducted using the MISEQ™ System (ILLUMINA®, San Diego, CA) according to the manufac-turer's instructions. Loading concentrations were 6-20 pM for Kit v3 and 6-10 pM for Kit v2 (300 cycle kit). Samples were 4-6 ng/μl (~10 nM).

C. Lambda Library Generation

Fragmentation

Up to 30 ug/g-TUBE (Covaris, Boston, England) of non-degraded, fully solubilized DNA in DI water or TE (10 mM Tris, 0.1 mM EDTA, pH 8.0) or 10 mM Tris-Cl, pH 8.5 having a starting size larger than 45 kbp is pre-warmed at room temperature (20° C. to 30° C.). The sample containing g-TUBE is centrifuged for 30 seconds at 13, 300 rpm (16,276 rcf (g)). Tubes are inverted and the centrifugation step repeated. Sheared DNA is recovered, reapplied to the upper chamber of the same g-TUBE, the centrifugation and inversion repeated twice, and the sheared DNA again recov-ered. Optionally, DNA is concentrated using a Zymo DNA concentration kit (Zymo; Irvine, CA). Final DNA concen-tration is measured using a Qubit fluorometer (Thermo Fisher Scientific, Carlsbad, CA). Alternatively, the average size of the fragmented gDNA is measured by loading 2 μl of the sample on a 1% agarose gel. Samples having an average size of ~6 kb are selected.

End Repair/dA-Tailing

End repair/dA-tailing is accomplished with an NEB-NEXT® ULTRA™ II End Repair kit (NEB, Ipswich, MA) after 1-2 ug of fragmented DNA is diluted to a final volume of 50 μl with EB buffer (10 mM Tris-Cl, pH 8.5). The final volume is 60 μl.

Ligation of dU-UMI Adapters

The molarity of the fragmented DNA and dU-UMI is calculated. DNA length of ~6 kb, 1 ug=0.25 pmol; 10 fold excess dU-UMI is 2.5 pmol; 100 fold excess dU-UMI is 25 pmol. A 10-100 molar excess of adapters are used. An appropriate amount (1-10 μl) of dU-UMI+T (Integrated DNA Technologies, Coralville, Iowa) overhang adapters are added to the 60 μl end repair/A-tailing mixture and then ligated using 1 μl Enhancer and 30 μl Ligation Mix from an NEBNEXT® ULTRA™ II Ligation kit (NEB, Ipswich, MA) prior to incubating for 15 minutes at 20° C.

SPRI Beads Purification

SPRI beads 1:0.8×(e.g. Beckman Coulter, Indianapolis, IN; Biocompare, South San Francisco, CA) were used according to the manufacturer's instructions and DNA eluted with 18 μl EB buffer for a sample recovery volume of 16-18 μl. Sample can then be stored at 4° C. for up to 72 hours or at −20° C. for longer periods.

dsDNA Fragmentase Reaction

A 16 μl sample of the SPRI purified DNA is digested using NEBNEXT® dsDNA Fragmentase (NEB, Ipswich, MA) according to the manufacturer's instructions but incu-bating at 37° C. for only 3.5-4 minutes. A 5 μl sample is optionally electrophoresed on a 1% agarose get to assess fragment size. Samples having an average size of 3 kb are selected and the volume adjusted to 50 μl with water.

The 50 μl digested DNA is purified using an SPRI bead ratio of 1:0.7× according to the manufacturer's instructions and eluted in 52 μl EB buffer to recover a volume of 50-52 μl.

End Repair

End repair is accomplished by adding the following components to 50 μl of the purified digested DNA: 6 μl CutSmart buffer (NEB, Ipswich, MA), 0.6 μl dNTPs (100 uM), 6 μl ATP (1 mM), 1 μl T4 polymerase, and 1 μl T4 PNK. Sample is incubated for 30-60 minutes at 20° C. SPRI purification is conducted using an SPRI bead ration of 1:1× according to the manufacturer's instructions and eluted in 52 μl for a recovery volume of 50-52 μl.

Figure 5:
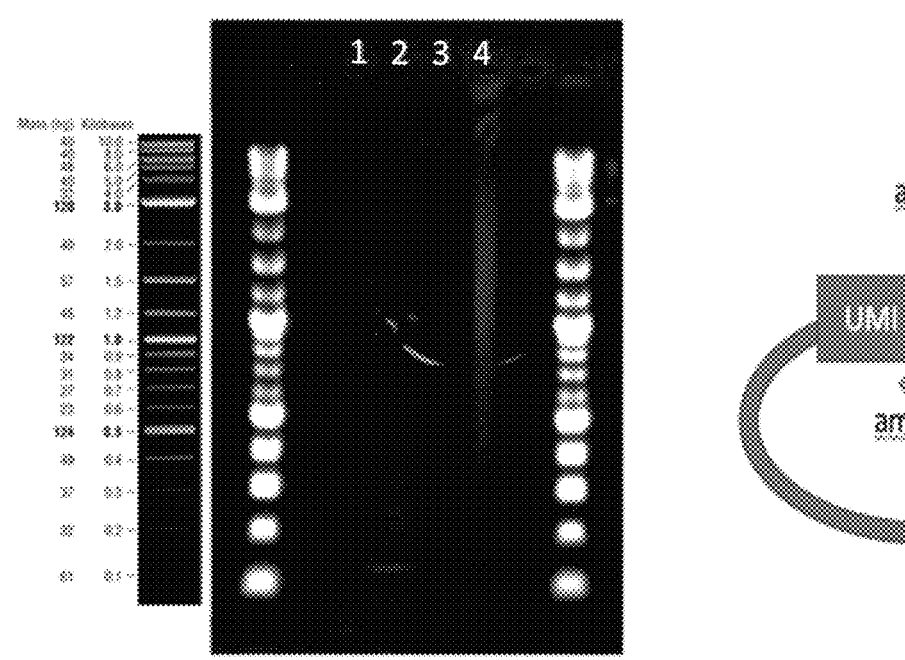
FIG. 5—Evidence of circularization. Lane 1: negative control (no DNA) pre-circularization; Lane 2, Lambda gDNA pre-circularization; Lane 3: negative control post-circularization; Lane 4: Lambda gDNA post-circularization.
Figure 6:
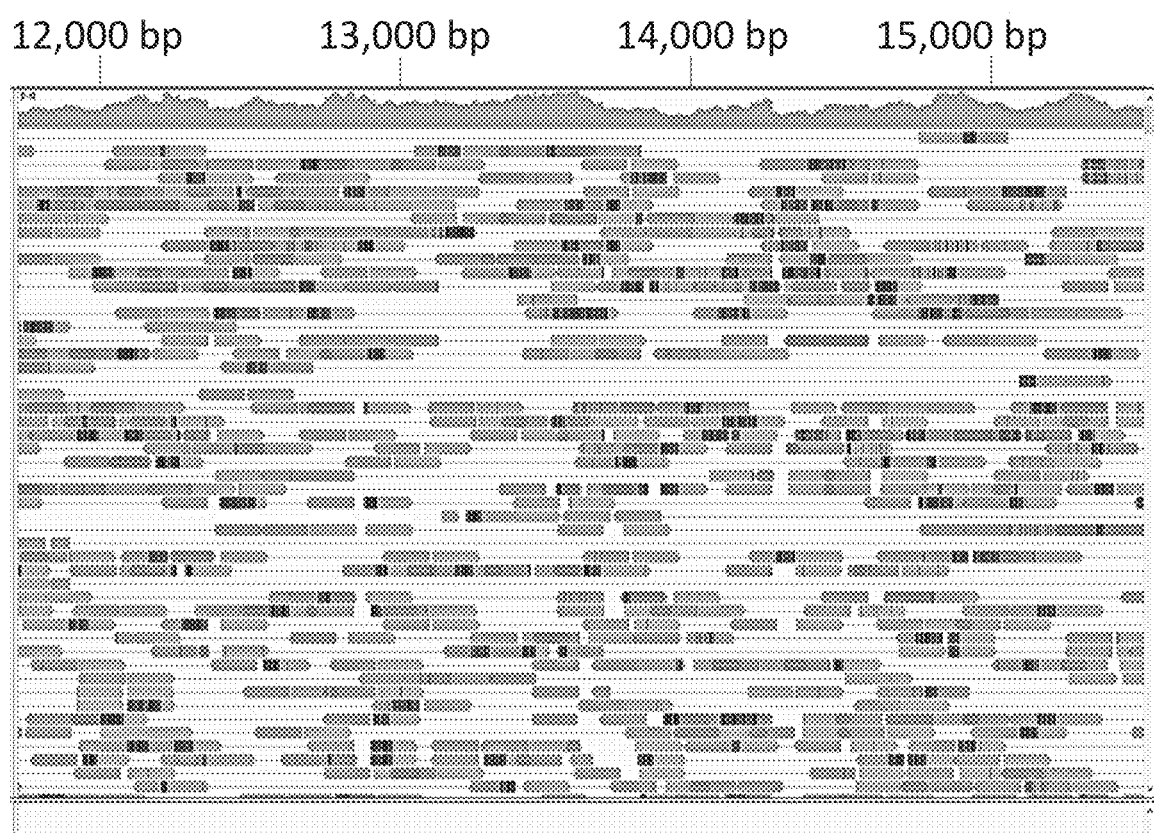
FIG. 6—Schematic of an Integrative Genomics Viewer (IGV) output showing paired reads aligned to a lambda genome and UMIs being properly incorporated/attached. UMIs are indicated by black bars.
Figures 7, 8:
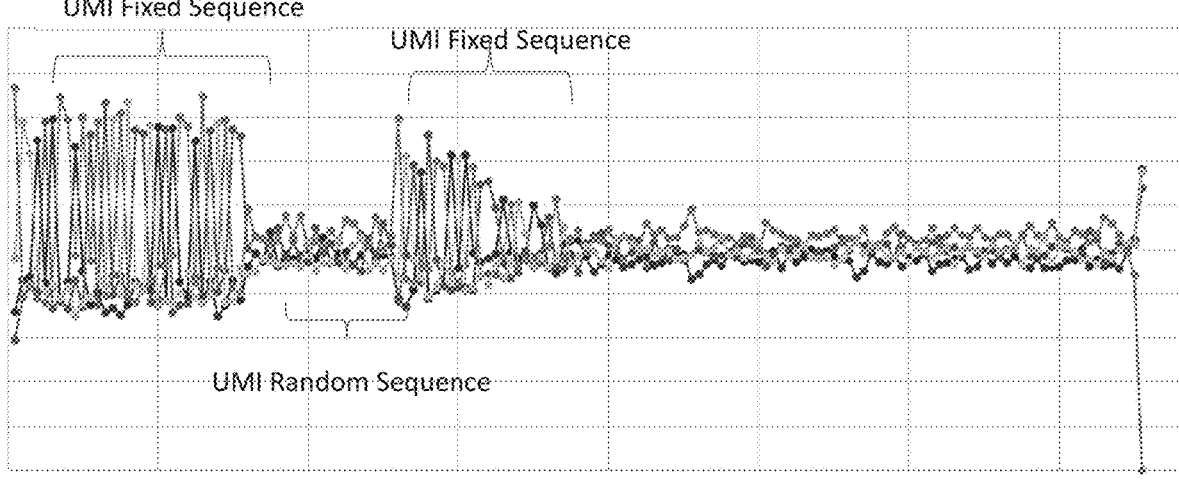
FIG. 7—Example of insert sizes and the extension sizes obtained from one end of the insert. Insert size is determined by subtracting the value in 5p from the value in 3p while extension size is determined by subtracting the value in End_1 from the value in End_2 for each paired read. Insert sizes from 500-1100 base pairs are extended by up to 129 base pairs, permitting a sequence read of about 1200 bp. Here, the extension comes from a second random primer binding to the same DNA fragment but in a different site and extends the sequence coverage. This Figure provides evidence that the extension of the sequence to create a long-read works on different size DNA fragments.
FIG. 8—Schematic showing the frequency of the four bases in the random UMI sequences. Each horizontal grid line is percent measured in increments of 5 and each vertical grid line is length measured in increments of 40 bp. Each of the four bases in the UMI Random Sequence portion of the read is present at about 25%, indicating that the UMIs are completely random and there is no bias.
Figure 9:
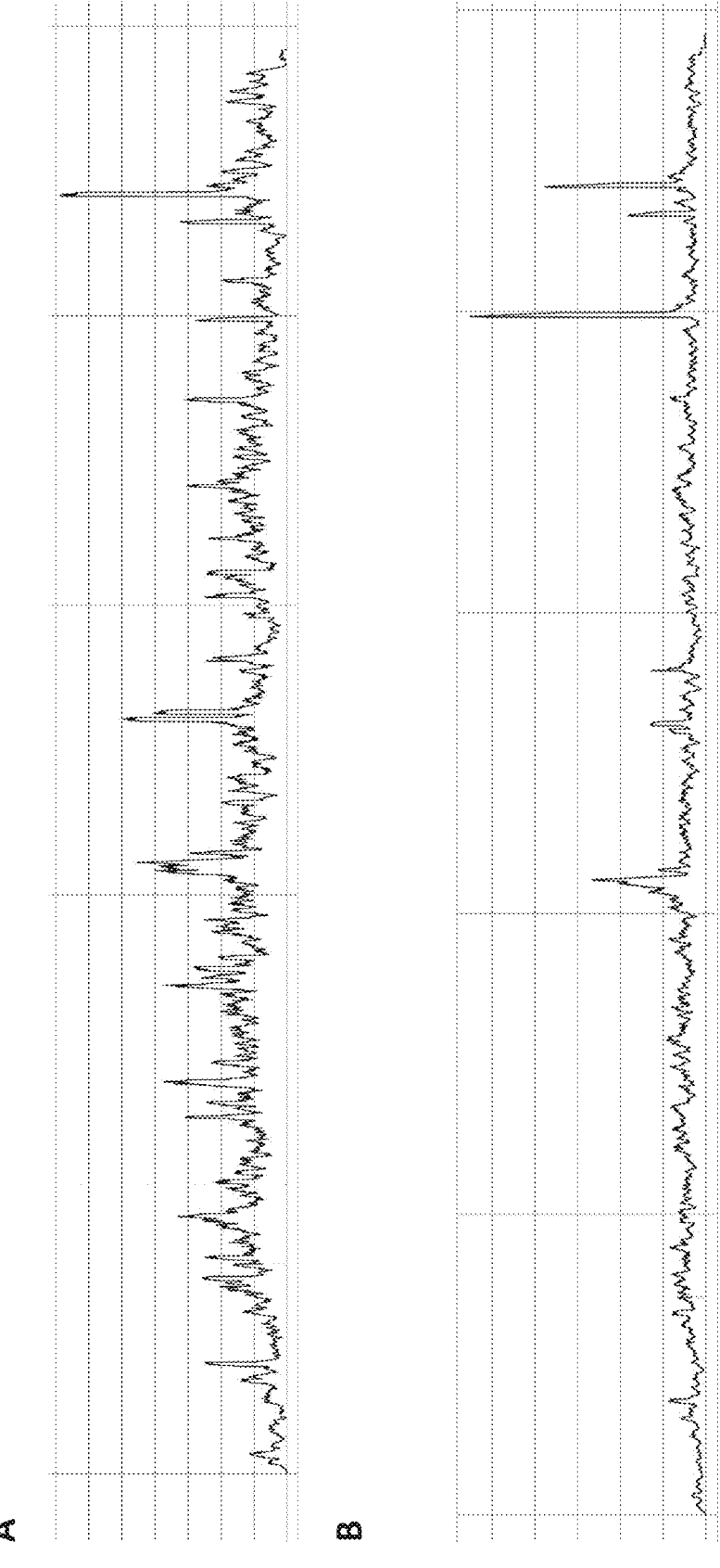
FIG. 9—Graph showing uniform coverage of the sequences for a 50 kb Lambda genome from two different libraries. Each horizontal grid line is the depth measured in increments of 25 and each vertical grid line is the position measured in increments of 10,000 bp. A: Library F4S; B: Library F4L.

Self-Circularization 150 ng of DNA, 15 µl ligase buffer and 3 µl Thermo T4 ligase (5U/µl; Thermo Fisher, Carlsbad, CA), 7.5 µl PEG 4000 (5%), and water are mixed for a final volume of 150 µl. The sample is incubated at 16-20° C. overnight and heat inactivated at 65° C. for 10 minutes. Any remaining linear DNA is removed by adding 2 µl Exonuclease I and 2 µl Exonuclease V prior to incubating at 37° C. for 1 hour. The exonucleases are inactivated by incubating at 75° C. for 20 minutes prior to SPRI purification using a bead ratio of 1:0.7× and eluting in 52 µl EB buffer for a recovery volume of 50-52 µl. To confirm that circularization occurred, additional sequences, used as primers, were added to the end of the dU-UMI adapters such that only the circularized DNA fragments could amplify a PCR reaction. The smear present in Lane 4 of FIG. 5 indicates the presence of circularized DNA.

USER+Fill-In

7 µl of NEBNEXT® ULTRA™ End Prep Reaction Buffer (NEB, Ipswich, MA) and 3 µl of USER enzyme (NEB, Ipswich, MA) is added to the self-circularized sample and incubated at 37° C. for 30 minutes prior to a 60° C. incubation for 5 minutes. 3 µl of NEBNEXT® ULTRA™ II End Prep Enzyme Mix (NEB, Ipswich, MA) is then added, the sample incubated for 30 minutes at 20° C., and then incubated for 30 minutes at 65° C.

Adapter Ligation 2.5 µl of 15 uM P5end duplex adapter compatible with T/A ligation is added to the USER+Fill-in sample along with 1 P5_duplex adapter Enhancer and 30 µl Ligation Mix from an NEBNEXT® ULTRA™ II Ligation kit (NEB, Ipswich, MA) prior to incubating for 15 minutes at 20° C. Sample is SPRI purified using a bead ratio of 1:0.85× according to manufacturer's instructions and eluting in 26 µl EB buffer for a recovery volume of 24-26 µl. A 2 µl sample is quantitated using a Qubit Fluorometer (Thermo Fisher, Carlsbad, CA).

Polymerase Mediated Primer Extension

The following primers were used in the polymerase mediated primer extension reactions: P7 extension V1 (5'→3') GGAGTTCAGACGTGTGCTCTTCC-GATCTNNNNNNNNNNNNN (SEQ ID NO:5) and P7 extension V2 (5'→3') GACTGGAGTTCA-GACGTGTGCTCTTCCGATCNNNNNNNNNNNNN (SEQ ID NO:6). 50 ng of DNA was used for each 10 µl reaction along with 2 µl dNTP mix, 1 µl SD DNA polymerase and 1 µl 10× enzyme buffer (Boca Scientific, Dedham, MA), and 2 µl of either the V1 or V2 primer. The sample is subjected to four cycles of incubation for 3 minutes at 92° C.; incubation for 5 minutes at 16° C.; and a 0.1° C./second ramp to 68° C. The sample was then extended at 68° C. for 15 minutes prior to holding at 4° C. This produces different sized molecules from the 3 kb fragment, all ending with the random UMI associated with that fragment, as illustrated in FIG. 4. The genome map is similarly generated from each continuous sequence or contig associated with each random UMI, as illustrated in FIG. 11.

The reaction was SPRI purified using a bead ratio of 1:0.9× according to manufacturer's instructions and eluted in 26 µl for a recovery volume of 24-26 µl. DNA concentration was measured using 2 µl of sample on a Qubit Fluorometer (Thermo Fisher, Carlsbad, CA) or, optionally, via electrophoresis.

MISEQ™ Sequencing

Sequencing was conducted using the MISEQ™ System (ILLUMINA®, San Diego, CA) according to the manufacturer's instructions. Loading concentrations were 6-20 pM for Kit v3 and 6-10 pM for Kit v2 (300 cycle kit). Samples were 4-6 ng/µl (~10 nM).

Examples of the results obtained are shown in FIG. 6-10.

Contig Formation

The individual reads are bioinformatically overlapped to generate longer contiguous sequences or contigs where each continuous sequence or contig is associated with a specific random UMI as illustrated in FIG. 4. Each UMI contig is then. bioinformatically overlapped to create a genome map or is compared to existing lambda genome sequences.

D. Targeted Sequencing of 16S Bacterial rDNA

PCR Amplification (Option 1)

Up to 100 ng/µl of non-degraded, fully solubilized DNA extracted from samples containing microbiomes or different bacterial species in DI water or TE (10 mM Tris, 0.1 mM EDTA, pH 8.0) or 10 mM Tris-Cl, pH 8.5 are used for amplification of 16S rDNA. Universal 16S rRNA bacterial primers 27F (5'-AGAGTTTGATCCTGGCTCAG-3' (SEQ ID NO: 7)) and 1392R (5'-GGTTACCTTGTTACGACTT-3' (SEQ ID NO:8)) or 8F (5'-TGGAGAGTTT-GATCCTGGCTCAG-3' (SEQ ID NO:9)) and 533R (5'-TACCGCGGCTGCTGGCAC-3' (SEQ ID NO:10)), or a different set of primers designed to amplify the bacterial 16S rDNA universally, are used to amplify this gene in a PCR reaction (Wang et al. (2018) AMB Expr 8:182). The forward or the reverse primer (only one primer) has a random UMI and the ILLUMINA® sequencing adapter sequence added to it. The PCR program is as follows: 95° C. for 5 min, 26 cycles at 95° C. for 60 s, 55° C. for 30 s, and 72° C. for 90 s, with a final extension of 72° C. for 10 min.

Sample is SPRI purified using a bead ratio of 1:0.85× according to manufacturer's instructions and eluted in 26 µl EB buffer for a recovery volume of 24-26 µl. A 2 µl sample is quantitated using a Qubit Fluorometer (Thermo Fisher, Carlsbad, CA).

Adapter Ligation 2.5 µl of 15 uM P5 and P3 end duplex adapter compatible with T/A ligation is added to the PCR product along with 1 P5 and P3_duplex adapter Enhancer and 30 µl Ligation Mix from an NEBNEXT® ULTRA™ II Ligation kit (NEB, Ipswich, MA) prior to incubating for 15 minutes at 20° C. Sample is SPRI purified using a bead ratio of 1:0.85× according to manufacturer's instructions and eluted in 26 µl EB buffer for a recovery volume of 24-26 µl. A 2 µl sample is quantitated using a Qubit Fluorometer (Thermo Fisher, Carlsbad, CA).

Polymerase Mediated Primer Extension

The following primers were used in the polymerase mediated primer extension reactions: P7 extension V1 (5'→3') GGAGTTCAGACGTGTGCTCTTCC-GATCTNNNNNNNNNNNNN (SEQ ID NO: 5) and P7 extension V2 (5'→3') GACTGGAGTTCA-GACGTGTGCTCTTCCGATCNNNNNNNNNNNNN (SEQ ID NO:6). 50 ng of DNA is used for each 10 µl reaction along with 2 µl dNTP mix, 1 µl SD DNA polymerase and 1 µl 10× enzyme buffer (Boca Scientific, Dedham, MA), and 2 µl of either the V1 or V2 primer. The sample is subjected to four cycles of incubation for 3 minutes at 92° C.; incubation for 5 minutes at 16° C.; and a 0.1° C./second ramp to 68° C. The sample is then extended at 68° C. for 15 minutes prior to holding at 4° C. This produces different sized molecules from the 16S rDNA fragment, all ending with the random UMI associated with that fragment, as illustrated in FIG. 14.

The reaction is SPRI purified using a bead ratio of 1:0.9× according to manufacturer's instructions and eluted in 26 µl for a recovery volume of 24-26 μl. DNA concentration was measured using 2 μl of sample on a Qubit Fluorometer (Thermo Fisher, Carlsbad, CA) or, optionally, via electrophoresis.

MISEQ™ Sequencing

Sequencing is conducted using the MISEQ™ System (ILLUMINA®, San Diego, CA) according to the manufacturer's instructions. Loading concentrations are 6-20 pM for Kit v3 and 6-10 pM for Kit v2 (300 cycle kit). Samples are 4-6 ng/μl (~10 nM).

Contig Formation

The individual reads are bioinformatically overlapped to generate longer contiguous sequences or contigs where each continuous sequence or contig is associated with a specific random UMI. Continuous sequences or contigs can then be compared to known 16S rDNA sequences for identification of bacterial species or variants, or can be used to as an identification tool for new species.

PCR Amplification (Option 2)

Up to 100 ng/μl of non-degraded, fully solubilized DNA extracted from samples containing microbiomes or different bacterial species in DI water or TE (10 mM Tris, 0.1 mM EDTA, pH 8.0) or 10 mM Tris-Cl, pH 8.5 is used for 16S rDNA amplification. Universal 16S rRNA bacterial primers 27F (5'-AGAGTTTGATCCTGGCTCAG-3' (SEQ ID NO: 7)) and 1392R (5'-GGTTACCTTGTTACGACTT-3' SEQ ID NO:8)) or 8F (5'-TGGAGAGTTTGATCCTGGCTCAG-3' SEQ ID NO:9)) and 533R (5'-TACCGCGGCT-GCTGGCAC-3' (SEQ ID NO:10)), or a different set of primers designed to amplify the bacterial 16S rDNA universally, are used to amplify this gene in a PCR reaction (Wang et al. (2018) AMB Expr 8:182). The forward or the reverse primer (only one primer) has a random UMI added to it. The PCR program is as follows: 95° C. for 5 min, 26 cycles at 95° C. for 60 s, 55° C. for 30 s, and 72° C. for 90 s, with a final extension of 72° C. for 10 min.

Sample is SPRI purified using a bead ratio of 1:0.85× according to manufacturer's instructions and eluted in 26 μl EB buffer for a recovery volume of 24-26 μl. A 2 μl sample is quantitated using a Qubit Fluorometer (Thermo Fisher, Carlsbad, CA).

Polymerase Mediated Primer Extension

The following primers are used in the polymerase mediated primer extension reactions: P7 extension V1 (5'→3') GGAGTTCAGACGTGTGCTCTTCCGATCTNNNNN-NNNNNNN (SEQ ID NO:5) and P7 extension V2 (5'→3') GACTGGAGTTCAGACGTGTGCTCTTCCGATCNN-NNNNNNNNN (SEQ ID NO:6). 50 ng of DNA is used for each 10 μl reaction along with 2 μl dNTP mix, 1 μl SD DNA polymerase and 1 μl 10× enzyme buffer (Boca Scientific, Dedham, MA), and 2 μl of either the V1 or V2 primer. The sample is subjected to four cycles of incubation for 3 minutes at 92° C.; incubation for 5 minutes at 16° C.; and a 0.1° C./second ramp to 68° C. The sample is then extended at 68° C. for 15 minutes prior to holding at 4° C. This produces different sized molecules from the 16S rDNA fragment, all ending with the random UMI associated with that fragment, as illustrated in FIG. 14.

The reaction is SPRI purified using a bead ratio of 1:0.9× according to manufacturer's instructions and eluted in 26 μl for a recovery volume of 24-26 μl. DNA concentration is measured using 2 μl of sample on a Qubit Fluorometer (Thermo Fisher, Carlsbad, CA) or, optionally, via electrophoresis.

MISEQ™ Sequencing

Sequencing is conducted using the MISEQ™ System (ILLUMINA®, San Diego, CA) according to the manufacturer's instructions. Loading concentrations are 6-20 PM for Kit v3 and 6-10 pM for Kit v2 (300 cycle kit). Samples are 4-6 ng/μl (~10 nM).

Contig Formation

The individual reads are bioinformatically overlapped to generate longer contiguous sequences or contigs where each continuous sequence or contig is associated with a specific random UMI. Continuous sequences or contigs can then be compared to known 16S rDNA sequences for identification of bacterial species or variants, or can be used to as an identification tool for new species.

The invention claimed is:

1. A method for generating a next generation sequencing library of any nucleic acid product comprising (a) isolating genomic DNA (gDNA), cDNA, or RNA from an organism;

(b) fragmenting the gDNA, cDNA, or RNA;

(c) isolating the gDNA, cDNA, or RNA fragments of step (b) and optionally conducting end-repair and/or A-tailing on each gDNA, cDNA, or RNA fragment;

(d) obtaining a collection of arbitrary and unique molecular identifier (UMI) adapters, each adapter comprising a different UMI flanked by at least one deoxyuracil (dU) with the form of dU/UMI/dU;

(e) attaching a different dU/UMI/dU adapter to each end of the gDNA, cDNA, or RNA fragment of step (c) to form a collection, wherein both ends of each gDNA, cDNA, or RNA fragment contains a dU/UMI/dU adapter to form dU/UMI/dU/gDNA/dU/UMI/dU fragments, dU/UMI/dU/cDNA/dU/UMI/dU fragments, or dU/UMI/dU/RNA/dU/UMI/dU fragments and wherein each end of the gDNA, cDNA, or RNA fragment of step (c) contains a different dU/UMI/dU adapter;

(f) fragmenting the collection of dU/UMI/dU/gDNA/dU/ UMI/dU fragments, dU/UMI/dU/cDNA/dU/UMI/dU fragments, or dU/UMI/dU/RNA/dU/UMI/dU fragments of step (e) into smaller fragments to form dU/UMI/dU/gDNA and gDNA/dU/UM/dU fragments, dU/UMI/dU/cDNA and cDNA/dU/UM/dU fragments, or dU/UMI/dU/RNA and RNA/dU/UM/dU fragments;

(g) optionally isolating the dU/UMI/dU/gDNA and gDNA/dU/UM/dU fragments, dU/UMI/dU/cDNA and cDNA/dU/UM/dU fragments, or dU/UMI/dU/RNA and RNA/dU/UM/dU fragments;

(h) diluting the dU/UMI/dU/gDNA and gDNA/dU/UM/dU fragments dU/UMI/dU/cDNA and cDNA/dU/UM/dU fragments, or dU/UMI/dU/RNA and RNA/dU/UM/dU fragments of step (f) or step (g), wherein the dilution prevents hetero-concaternerization;

(i) self-ligating each of the dU/UMI/dU/gDNA, gDNA/dU/UM/dU, dU/UMI/dU/cDNA, cDNA/dU/UM/dU, dU/UMI/dU/RNA, or RNA/dU/UM/dU fragments of step (h) to form circular molecules;

(j) contacting the self-ligated circular molecules of (i) with a USER enzyme to create a linear gDNA, cDNA, or RNA, wherein each end of the USER treated gDNA, cDNA, or RNA has the same UMI at each end;

(k) conducting end-repair on the USER treated linear gDNA, cDNA, or RNA of step (j);

(l) ligating sequencing adapters comprising sequencing primers and index sequences to each end of the linear gDNA, cDNA, or RNA of step (k);

(m) performing PCR extension on the linear gDNA, cDNA, or RNA from step (l), using deoxynucleotide triphosphates (dNTPs) only to obtain a collection of PCR products using (i) a first collection of forward primers, wherein each forward primer comprises in 5' to 3' order a first sequencing adapter tail, a random unique molecular identifier (UMI), which will serve as a starting sequence point in a de novo assembly of the nucleic acid interest, and a sequence specific to the nucleic acid of interest; and (ii) a collection of reverse primers, wherein each reverse primer consists of a sequence specific to the nucleic acid of interest;

(n) performing PCR primer extension on the collection of PCR products of step (m) to obtain a collection of double stranded PCR primer extension products using (i) a second collection of forward primers comprising in 5' to 3' order a second forward primer sequencing adapter tail and a random primer sequence; and (ii) a reverse primer consisting of the first sequencing adapter tail as set forth in step (m)(i);

(o) isolating the collection of double stranded PCR primer extension products of step (n) for sequencing;

(p) sequencing the isolated collection of double stranded PCR primer extension products of step (o), wherein the sequencing results in a collection of sequences and wherein one of the sequences of the collection of sequences comprises the random UMI;

(q) identifying the sequence comprising the random UMI obtained from the sequencing of step (p); and (r) overlapping each sequence of the collection of sequences obtained from step (p) to form a contiguous sequence, wherein the sequence which comprises the random UMI identified in step (q) is used as a starting point for forming the contiguous sequence.

2. The method according to claim 1, wherein the fragments of step (b) are approximately 5-8 kb in length.

3. The method according to claim 1, wherein the dU/UMI/dU/gDNA and gDNA/dU/UM/dU fragments, dU/UMI/dU/cDNA and cDNA/dU/UM/dU fragments, or dU/UMI/dU/RNA and RNA/dU/UM/dU fragments of step (f) are 2-4 kb in length.

4. A method for generating a genomic map of an organism without reliance on a reference sequence comprising preparing a next generation sequencing library of PCR products according to claim 1, wherein gDNA is used and the first collection of forward primers of step (m)(i) is replaced with a collection of forward primers comprising in 5' to 3' order a first sequencing adapter tail, a random unique molecular identifier (UMI), which will serve as a starting sequence point in a de novo assembly of the nucleic acid of interest, and a random sequence, and the collection of reverse primers of step (m)(ii) is replaced with a collection of revers primers, wherein each reverse primer consists of a random sequence.

5. A method for generating a next generation sequencing library of any nucleic acid product comprising (a) isolating genomic DNA (gDNA), cDNA, or RNA from an organism;

(b) fragmenting the gDNA, cDNA, or RNA;

(c) isolating the gDNA, cDNA, or RNA fragments of step (b) and optionally conducting end-repair and/or A-tailing on each gDNA, cDNA, or RNA fragment;

(d) obtaining a collection of arbitrary and unique molecular identifier (UMI) adapters, each adapter comprising a different UMI flanked by at least one deoxyuracil (dU) with the form of dU/UMI/dU;

(e) attaching a different dU/UMI/dU adapter to each end of the gDNA, cDNA, or RNA fragment of step (c) to form a collection, wherein both ends of each gDNA, cDNA, or RNA fragment contains a dU/UMI/dU adapter to form dU/UMI/dU/gDNA/dU/UMI/dU fragments, dU/UMI/dU/cDNA/dU/UMI/dU fragments, or dU/UMI/dU/RNA/dU/UMI/dU fragments, wherein each end of the gDNA, cDNA, or RNA fragment of step (c) contains a different dU/UMI/dU adapter;

(f) fragmenting the collection of dU/UMI/dU/gDNA/dU/ UMI/dU fragments, dU/UMI/dU/cDNA/dU/UMI/dU fragments, or dU/UMI/dU/RNA/dU/UMI/dU fragments into smaller fragments to form dU/UMI/dU/ gDNA and gDNA/dU/UM/dU fragments, dU/UMI/dU/ cDNA and cDNA/dU/UM/dU fragments, or dU/UMI/ dU/RNA and RNA/dU/UM/dU fragments;

(g) optionally isolating the dU/UMI/dU/gDNA and gDNA/dU/UM/dU fragments, dU/UMI/dU/cDNA and cDNA/dU/UM/dU fragments, or dU/UMI/dU/RNA and RNA/dU/UM/dU fragments;

(h) diluting the dU/UMI/dU/gDNA and gDNA/dU/UM/ dU fragments dU/UMI/dU/cDNA and cDNA/dU/UM/ dU fragments, or dU/UMI/dU/RNA and RNA/dU/UM/ dU fragments of step (f) or step (g), wherein the dilution prevents hetero-concaternerization;

(i) self-ligating each of the dU/UMI/dU/gDNA, and gDNA/dU/UM/dU, fragments, dU/UMI/dU/cDNA, and cDNA/dU/UM/dU, or dU/UMI/dU/RNA, and RNA/dU/UM/dU fragments of step (h) to form a collection of circular molecules;

(j) fragmenting the collection of circular molecules of step (i) to create a collection of linear gDNA, cDNA, or RNA molecules, wherein the dU/UMI/dU is internal to the two ends of each linear molecule;

(k) contacting the collection of linear molecules of step (j) with a USER enzyme to cleave the dU/UMI/dU sequence and to create two linear gDNA, cDNA, or RNA fragments from each linear molecule in the collection;

(l) conducting end-repair on the USER treated linear gDNA, cDNA, or RNA fragments of step (k);

(m) ligating sequencing adapters comprising sequencing primers and, optionally, index sequences to each end of the linear gDNA, cDNA, or RNA fragments of step (l);

(n) performing PCR extension on the linear gDNA, cDNA, or RNA fragments from step (m), using deoxynucleotide triphosphates (dNTPs) only to obtain a collection of PCR products using (i) a first collection of forward primers, wherein each forward primer comprising in 5' to 3' order a first sequencing adapter tail, and a random unique molecular identifier (UMI), which will serve as a starting sequence point in a de novo assembly of the nucleic acid of interest, and a sequence specific to the nucleic acid of interest, and (ii) a collection of reverse primers, wherein each reverse primer consists of a sequence specific to the nucleic acid of interest;

(o) performing PCR primer extension on the collection of PCR products step (n) to obtain a collection of double stranded PCR primer extension products using (i) a second collection of forward primers comprising in 5' to 3' order a second forward primer sequencing adapter tail and a random primer sequence; and (ii) a reverse primer consisting of the first sequencing adapter tail as set forth in step (m)(i);

(p) isolating the collection of double stranded PCR primer extension products of step (o) for sequencing;

(q) sequencing the isolated collection of double stranded PCR primer extension products of step (o), wherein the sequencing results in a collection of sequences and wherein one of the sequences of the collection of sequences comprises the random UMI;

(r) identifying the sequence comprising the random UMI obtained from the sequencing of step (q); and (s) overlapping each sequence of the collection of sequences obtained from step (q) to form a contiguous sequence, wherein the sequence which comprises the random UMI identified in step (r) is used as a starting point for forming the contiguous sequence.

6. The method according to claim 5, wherein the fragments of step (b) are approximately 5-8 kb in length.

7. The method according to claim 5, wherein the dU/UMI/ dU/gDNA and gDNA/dU/UM/dU fragments, dU/UMI/dU/ cDNA and cDNA/dU/UM/dU fragments, or dU/UMI/dU/ RNA and RNA/dU/UM/dU fragments of step (f) are 2-4 kb in length.

8. The method according to claim 5, wherein the first collection of forward primers of step n(i) corresponds to sequences from a reference genome.

9. A method for generating a genomic map of an organism comprising (a) preparing a next generation sequencing library according to claim 5; and (b) comparing the contiguous sequence of step (s) to a reference genome.

10. A method for generating a virtual karyotype for an organism comprising (a) generating a genomic map for the organism according to claim 9;

(b) comparing the genomic map from step (a) to a reference genomic map of the organism's chromosomes;

(c) identifying the genomic sequences associated with each chromosome; and (d) identifying any chromosomal abnormalities in the genomic map of step (a) as compared to the reference genomic map.

11. The method according to claim 10, wherein the chromosomal abnormality is a translocation.

12. The method according to claim 10, wherein the chromosomal abnormality is identification of a sequence insertion and/or deletion.

13. The method according to claim 10, wherein the chromosomal abnormality is a sequence variation and/or a sequence copy number variation (CNV).

14. The method according to claim 10, wherein the chromosomal abnormality is a chromosomal rearrangement.

* * * * *

SEQUENCE LISTING

```
Sequence total quantity: 12
SEQ ID NO: 1          moltype =    length =
SEQUENCE: 1
000

SEQ ID NO: 2          moltype =    length =
SEQUENCE: 2
000

SEQ ID NO: 3          moltype = DNA  length = 37
FEATURE               Location/Qualifiers
misc_feature          1..37
                      note = Truncated P7 adapter
source                1..37
                      mol_type = other DNA
                      organism = synthetic construct
SEQUENCE: 3
gggggactg gagttcagac gtgtgctctt ccgatc                        37

SEQ ID NO: 4          moltype = DNA  length = 36
FEATURE               Location/Qualifiers
misc_feature          1..36
                      note = Truncated P7 adapter
source                1..36
                      mol_type = other DNA
                      organism = synthetic construct
SEQUENCE: 4
gatcggaaga gcacacgtct gaactccagt caaaaa                       36
```

-continued

```
SEQ ID NO: 5              moltype = DNA   length = 40
FEATURE                   Location/Qualifiers
misc_feature              1..40
                          note = Primer for P7 extension
source                    1..40
                          mol_type = other DNA
                          organism = synthetic construct
SEQUENCE: 5
ggagttcaga cgtgtgctct tccgatctnn nnnnnnnnn                         40

SEQ ID NO: 6              moltype = DNA   length = 43
FEATURE                   Location/Qualifiers
misc_feature              1..43
                          note = Primer for P7 extension
source                    1..43
                          mol_type = other DNA
                          organism = synthetic construct
SEQUENCE: 6
gactggagtt cagacgtgtg ctcttccgat cnnnnnnnnn nnn                    43

SEQ ID NO: 7              moltype = DNA   length = 20
FEATURE                   Location/Qualifiers
misc_feature              1..20
                          note = 16S rDNA Universal Bacterial Primer 27F
source                    1..20
                          mol_type = other DNA
                          organism = synthetic construct
SEQUENCE: 7
agagtttgat cctggctcag                                             20

SEQ ID NO: 8              moltype = DNA   length = 19
FEATURE                   Location/Qualifiers
misc_feature              1..19
                          note = 16S rDNA Universal Bacterial Primer 139R
source                    1..19
                          mol_type = other DNA
                          organism = synthetic construct
SEQUENCE: 8
ggttaccttg ttacgactt                                              19

SEQ ID NO: 9              moltype = DNA   length = 23
FEATURE                   Location/Qualifiers
misc_feature              1..23
                          note = 16S rDNA Universal Bacterial Primer 8F
source                    1..23
                          mol_type = other DNA
                          organism = synthetic construct
SEQUENCE: 9
tggagagttt gatcctggct cag                                         23

SEQ ID NO: 10             moltype = DNA   length = 18
FEATURE                   Location/Qualifiers
misc_feature              1..18
                          note = 16S rDNA Universal Bacterial Primer 533R
source                    1..18
                          mol_type = other DNA
                          organism = synthetic construct
SEQUENCE: 10
taccgcggct gctggcac                                               18

SEQ ID NO: 11             moltype = DNA   length = 110
FEATURE                   Location/Qualifiers
source                    1..110
                          mol_type = genomic DNA
                          organism = Homo sapiens
SEQUENCE: 11
attttttttt tttttttttg aaatggagtc tcgctctgtt gcccaggctg gagtgccttc  60
aaaaaggcaa ttgattagtt tcagcttttc caaaccgaga tccgatatgt            110

SEQ ID NO: 12             moltype = DNA   length = 106
FEATURE                   Location/Qualifiers
source                    1..106
                          mol_type = genomic DNA
                          organism = Homo sapiens
SEQUENCE: 12
gtagtaaaaa ccatcagtag ggtcgaagtt caactaattg ctttttttcg tttacccatc  60
ggtgggtata tcgagagatg aaatttgttt taaattttaa gtccca               106
```